(12) United States Patent
Richardson et al.

(10) Patent No.: US 6,989,397 B1
(45) Date of Patent: Jan. 24, 2006

(54) IRON CHELATORS AND USES THEREOF

(75) Inventors: Des Richardson, Quakers Hill (AU); Paul Vincent Bernhardt, Chapel Hill (AU); Erika Michelle Becker, Moorooka (AU)

(73) Assignees: University of Queensland, Brisbane (AU); The Heart Research Institute Ltd., Camperdown (AU)

( * ) Notice: Subject to any disclaimer, the term of this patent is extended or adjusted under 35 U.S.C. 154(b) by 126 days.

(21) Appl. No.: 10/069,923

(22) PCT Filed: Sep. 4, 2000

(86) PCT No.: PCT/AU00/01050

§ 371 (c)(1),
(2), (4) Date: May 10, 2002

(87) PCT Pub. No.: WO01/17530

PCT Pub. Date: Mar. 15, 2001

(30) Foreign Application Priority Data
Sep. 2, 1999 (AU) .................................. PQ2624

(51) Int. Cl.
*C07D 213/02* (2006.01)
*C07D 401/02* (2006.01)
*A61K 31/47* (2006.01)

(52) U.S. Cl. .................. 514/352; 514/332; 514/336; 514/342; 546/255; 546/283.4; 546/309

(58) Field of Classification Search ............ 546/268.7, 546/269.1, 269.4, 269.7, 271.1, 271.4, 283.5, 546/255, 309; 514/339, 332, 336, 342, 352
See application file for complete search history.

(56) References Cited

U.S. PATENT DOCUMENTS

| | | | |
|---|---|---|---|
| 5,011,932 A | 4/1991 | Rector et al. | |
| 5,023,334 A | 6/1991 | Rector et al. | |
| 5,229,038 A | 7/1993 | Uchino et al. | |
| 6,005,009 A | 12/1999 | Murad et al. | |

FOREIGN PATENT DOCUMENTS

| | | |
|---|---|---|
| DE | 4207400 A1 | 9/1993 |
| EP | 0 879 606 A1 | 11/1998 |
| WO | WO 86/04582 A1 | 8/1986 |
| WO | WO 98/41198 A1 | 9/1998 |
| WO | WO 98/48848 A1 | 11/1998 |
| WO | WO 99/01423 A1 | 1/1999 |

OTHER PUBLICATIONS

Richardson et. al., "Iron Chelators for the treatment of Iron Overload Disease: Relationship Between Structure, Redox Activity and Toxicity", American Journal of Hematology 73: 200-210 (2003).*

Ca 139: 190384, "Friedreich's ataxia: iron chelators that target the mitochondrion as a therapeutic strategy?", Richardson, D. R.*

Fujuikawa et al, Chemical Abstracts 72:110,952, May 12, 1984.*

Pal, et al., "Copper (II) complexes containing a CuN4O2 coordination sphere assembled via pyridine-imine-amide coordination: Synthesis, structure and properties," Abstract No.: 2000:615159.

Sangeetha, et al., "Dimeric and polymeric square-pyramidal copper (II) complexes containing equatorial-apical chloride or acetate bridges," Abstract No. 2000:586466.

Paschalidis, et al., "Synthesis, characterization and spectra of lanthanide (III) hydrazone complexes. The x-ray molecular structures of the erbium (III) complex and the ligand," Abstract No. 2001:23264.

Richardson et al., "Development of potential iron chelators for the treatment of Friedreich's ataxia: ligands that mobilize mitochondrial iron," Abstract No. 2001: 429212.

Pal, et al., "Mononuclear pervanadyl (VO2+) complexes with tridentate Schiff bases: self-assembling via c-H . . . oxo and $\pi$—$\pi$ interactions," Abstract No. 2001:516573.

Heuer et al., "Preparation of pyridyl acylhydrazones as microbicides," Abstract No. 1994:106782.

Rector et al., "Anthelmintic pyridinyl acylhydrazones," Abstract No.: 1987:477634.

Alberto et al., "Method for the preparation of facial metal tricarbonyl compounds and their use int he labeling of biologically active substrates," Abstract No.: 1998:719299.

Choudhury, Amitava et al., "Synthesis, structure and properties of manganese (II) complexes with aroylhydrazones of 2-pyridine-carboxaldehyde." Abstract No. 2000:269511.

Registry No. 1215-55-0/RN—Benzoic acid, (2-pyridinylmethylene) hydrazide.

Registry No. 270576-10-8/RN—Benzoic acid, (2E)-(2-pyridinylmethylene) hydrazide.

(Continued)

*Primary Examiner*—Zinna Northington Davis
(74) *Attorney, Agent, or Firm*—Rothwell, Figg, Ernst & Manbeck

(57) ABSTRACT

The present invention provides 2-pyridylcarboxaldehyde isonicotinoyl hydrazone (PCIH) analogues suitable for use as an in vivo iron chelators, the PCIH analogue having Formula 1:

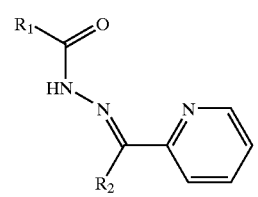

Formula 1 wherein R1 is an aromatic or heterocyclic group and R2 is either H or OH; isomers thereof or salts thereof; pharmaceutical compositions containing the analogues; and uses of the analogues in the treatment of iron-overload diseases.

10 Claims, 9 Drawing Sheets

OTHER PUBLICATIONS

Registry No. 114011-30-2/RN—2-Thiophenecarboxylic acid, (2-pyridinylmethylene) hydrazide.

Registry No. 262421-84-1—Benzoic acid, 3-bromo-(2-pyridinylmethylene) hydrazide.

Registry No. 270576-18-6/RN—2-Thiophenecarboxylic acid, (2E)-(2-pyridinylmethylene) hydrazide.

Registry No. 257299-43-7/RN—Benzoic acid, (2E)-(2-pridinylmethylene) hdyrazide, monohydrate.

Registry No. 264876-19-9/RN—Benzoic acid, (2Z)-(2-pyridinylmethylene) hydrazide.

Registry No. 262421-84-1/RN—Benzoic acid, 3-bromo-, (2-pyridinylmethylene) hydrazide.

Becker et al., "Development of novel aroylhydrazone ligands for iron chelation therapy; 2-pyridylcarboxaldehyde isonicotinoyl hydrazone analogs," *The Journal of Laboratory and Clinical Medicine*, 1999, pp. 510-521, vol. 134, No. 5, C.V. Mosby.

Ainscough et al., "Cytotoxicity of salicylaldehyde benzoylhydrazone analogs and their transition metal complexes: quantitative structure-activity relationships," *Journal of Inorganic Biochemistry*, 1999, pp. 125-133, vol. 77, Nos. 3-4, Elsevier Science Inc.

Richardson et al., "The biologically active iron chelators 2-pyridylcarboxaldehyde isonicotinoylhydrazone, 2-pyridylcarboxaldehyde benzoylhydrazone monohydrate and 2-furaldehyde isonicotinoylhydrazone," *Acta Crystallographia*, 1999, pp. 2102-2105, vol. C55, No. 12, Munksgaard International publishers Ltd., Great Britain.

Gallego et al., "Pyridine-2-carbaldehyde 2-Hydroxybenzoylhydrazone as a Selective Reagent for the Extraction and Spectrophotometric Determination of Iron (II)," *Analyst*, Jul., 1979, pp. 613-619, vol. 104, London, U.K.

Iki et al., "2-Pyridylaldehydebenzoylhydrazone Derivatives as Highly Selective Precolumn Chelating Reagents for Nickel (II) Ion I Kinetic Differentiation Mode High-Performance Liquid Chromatography," *Mikrochim Acta*, 1994, 137-52, vol. 113(3-6), Springer-Verlag, Austria.

Ponka et al., "The Effect of various chelating agents on the mobilization iron from reticulocytes in the presence and absence of pyridoxal isonicotinoyl hydrazone," *Biochem. Biophys Acta*, 1984, pp. 477-489, vol. 802(3), Elsevier Science Publishers B.V.

Gimenez Plaza, et al., The Synthesis, Identification and Reactivity of 2-Pyridylaldehyde 2-Thiophenehydrazide, and a Study of the Solid Complexes Formed with Pb (II), Cu (II), Ag (I), Ni (II) and Co (II), *Anales de Quimica*, 1987, pp. 288-292, vol. 83, (English Translation).

Duggal et al., "Synthesis and structural studies of chlorobenzoyl and salicyloylhydrazone complexes of tridentate hydrazones," Chemical Abstract No. 110:107066t, vol. 110, No. 12, Mar. 20, 1989.

Uehra et al., "Comparison of hydrazone derivatives for reversed phase high performance liquid chromatography," Chemical Abstract No. 120:314578h, vol. 120, No. 24, Jun. 13, 1994.

Mautoiu et al., "Pyridine-2-aldehyde-2-furoylhydrazone—a new visualization Reagent for cation separation by TLC," Chemical Abstract No. 125:157099m, vol. 125, No. 12, Sep. 16, 1996.

Zhao et al., "Hydrazide-Containing Inhibitors of HIV-1 Integrase," Chemical Abstract No. 126:194859a, vol. 126, No. 15, Apr. 14, 1997.

Nishimoto et al., "Thin-layer chromatography of chelating agents," 1967, Abstract No. 1967:98544.

Davies et al., "Minimization of the rate of ambient dioxygen consumption by a coal-derived middle distillate," Abstract No. 1986:594226.

Gimenez Plaza et al., 2-Pyridylaledhye 2-thenoylhydrazone: synthesis, identification and reativity. Study of solid complexes with lead (II), copper (II), silver (I), nickel (II) and cobalt (II), Abstract No. 1988-197186.

Hoshino, et al., "Kinetic differentiation mode high-performance liquid chromatography as a powerful tool in environmental trace metal chemistry," Abstract No.: 1995: 583241.

Iki et al., "2-Pyridylaledyde benzoylhydrazone derivatives as highly selective precolumn chelating reagents for nickel (III) ion in kinetic differentiation," Abstract No. 1994: 670602.

Uehra et al., "Comparison of hydrazone derivatives for reversed phase high performance liquid chromatography," Abstract No.: 1994:314578.

Khalil et al., Organotin (IV) complex with tridentate ligands-II, Synthesis and characterization of mono- and dimethyltin (IV) complexes with N-(2-pyridinylmethylene) benzoylhydrazine. The crystal and molecular structure of monomethyldichloroN-(2-pyridinylmethylene) benzoylhydrazinate NNO(-1)tin(IV), Abstract No. 1994:700990.

Ainscough et al., "Nitrogen, sulfur and oxygen donor adducts with copper (II) complexes of antitumor 2-formylpyridinethiosemicabazone analogs: physicohemical and cytotoxic studies." Abstract No. 1998-541058.

Becker et al., "Development of novel roylhydrazone ligands for iron chelation therapy: 2-pyridylcarboxaldehyde isonicotinoyl hydrazone analogs," Abstract No. 1999:783045.

Richardson et al., "The biologically active iron chelators 2-pyridylcarboxaldehyde isonicotinoylhydrazone, 2-pyridylcarboxaldehyde benzoylhydrazone monohydrateand 2-furaldehyde isonicotinoylhydrazone," Abstract No.: 2000; 42711.

Lima et al., "Synthesis and analgesic activity of novel N-acylarylhydrazones and isosters, derived from natural safrole," Abstract No. 2000:228176.

Pelagatti et al., "Potentially tridentate hydrazonic ligands in the synthesis of methyl and acetyl palladium (II) complexes," Abstract No.: 2000:193344.

Karunakar, et al., Nickel (II) complexes of tridentate N,N, O-donor ligands: syntheses, structures and redox properties. Abstract No. 2000:414118.

Aboul Wafa et al., "Novel Benzol[b]thienylhydrazine and 1,3,4-Oxadiazole Derivatives as Potential Antidepressant Agents," *Arch Pharm. (Weinheim)*, 1992, pp. 603-608, vol. 325.

Iyer et al., "p-Aminosalicylic Acid Derivatives as Possible Tuberculostats," *Indian Journal of Chemistry*, Nov. 1970, pp. 964-968, vol. 8.

Komurcu, S.G, et al., "Evaluation of some arylhydrazones of p-aminobenzoic acid hydrazide as antimicrobial agents and their in vitro hepatic microsomal metabolism," *Boll. Chim. Farmaceutico*, 1995, pp. 375-379, vol. 134, No. 7.

Lima et al., "Synthesis and analgesic activity of novel N-acylarylhydrazones and isosters, derived from natural safrole," *Eur. J. Med. Chem.*, 2000, pp. 187-203, vol. 35.

Richardson, Des R., "Analogues of Pyridoxal Isonicotinoyl Hydrazone (PIH) as Potential Iron Chelators for the Treatment of Neoplasia," *Leukemia and Lymphoma*, 1998, pp. 47-60, vol. 31, No. 1-2.

Capitan et al., "Spectra and reactivity with inorganic ions of 2-pyridylaldehyde 2-quinolylhydrazone, 2-pyridylaldehyde 2-quinolylcarbonylhydrazone, and 6-methyl-2-pyridylaldehyde 2-quinolylcarbonylhydrazone," Chemical Abstract No. 84:11787, 1975 (from *ARS Pharmaceutica* (1975) 16(2), pp. 293-304).

* cited by examiner

IRON CHELATORS AND USES THEREOF

TECHNICAL FIELD

The present invention relates to compounds which are capable of chelating iron and having use in addressing or treating iron-overload situations.

BACKGROUND ART

Iron (Fe) is the most abundant metal ion found in cells, reflecting its crucial roles in the oxidation-reduction reactions upon which life depends. The rich and unique chemistry of Fe has endowed it with properties absolutely essentially for oxygen transport, ATP production and DNA synthesis. These characteristics which make Fe an obligate requirement for life also make it a potential target for preventing the growth of neoplastic cells.

In order to understand the role of Fe in cellular proliferation and the possible use of Fe chelators as effective antitumour agents, it is important to describe how this metal ion is transported and metabolised in normal and neoplastic cells. This is described at length in a review article entitled "Potential of Iron Chelators as Effective Anti-proliferative Agents" by D. R. Richardson which is published 1997 in Can J. Physiol. Pharmacol. 75 1164–80 and which is incorporated herein by reference.

References is also made to "Analogues of Pyridoxal Isonicotinoyl Hydrazone (PIH) as Potential Iron Chelators for the Treatment of Neoplastia" by D. R. Richardson reported at Leukaemia and Lymphoma. 1998, 31 47–60 which is also incorporated herein by reference and from which most of the following discussion has been taken.

Transportation of Fe in the serum is performed by the glycoprotein transferrin (Tf), which binds two atoms of Fe(III). Transferrin donates its Fe to cells by binding to specific Tf receptors (TfR) on the cell membrane. Upon binding to the TfR, the Tf-TfR complex is internalized within endocytotic vesicles and the Fe released from the protein by a decrease in the intravescular pH to 5.5. Apart from the specific receptor-mediated process of Fe uptake from Tf, another process consistent with non-specific adsorptive pinocytosis has also been reported in rat hepatocytes, human hepatoma cells and human melanoma cells. Once the Fe is released from Tf, it is then bound by a specific membrane transporter that remains uncharacterized. Recently, a possible candidate for this latter protein has been identified, namely the product of the gene Nramp2. This molecule has been called the divalent cation transport 1 (DCT1), and may be involved in both Fe absorption from the gut and also Fe transport across the endosomal membrane. Once Fe is transported across the membrane, it then enters a poorly characterized compartment known as the intracellular Fe pool. The identity of the pool is highly controversial and may be composed of low $M_r$ Fe complexes of citrate, amino acids and nucleotides or alternatively, the Fe may be bound to high $M_r$ macromolecules. Experiments have shown that the pool is composed of molecules containing Fe in the Fe(II) and Fe(III) oxidation states. In some cells, such as developing erythroid precursors, the low $M_r$ weight Fe pool represents only a very small fraction of the total amount of Fe in the cell, whereas in other cell types, such as Chang cells, it may represent a considerably proportion of the total Fe present. Iron in the pool can be used for incorporation into Fe-containing proteins, such as the cytochromes and Fe-S proteins, and when in excess, Fe can be incorporated into the Fe storage protein ferritin.

The role played by Fe in cellular proliferation has been well demonstrated in numerous studies. For example, in the absence of Fe, ribonucleotide reductase cannot produce deoxyribonucleotides and this has a profound effect on the cell cycle resulting in a $G_1/S$ block which can lead to apoptosis. Cancer cells express very high levels of the transferring receptor (TfR), suggesting that they have a high Fe requirement. In fact, in vivo, some neoplastic cell types take up Fe from Tf at a rate that is comparable to hemoglobin producing cells such as reticulocytes. It is of interest that the host may withhold Fe during neoplastic cell proliferation, and this is found in Hodgkins and non-Hodgkins lymphoma where there is a pronounced decrease in the saturation of Tf with Fe. This latter phenomenon is known as the hypoferremic shift, which has been suggested to be a physiological response to hinder tumor cell growth. The importance of the TfR in Fe uptake and cell proliferation is demonstrated by the fact that the monoclonal antibody 42/6 which blocks the binding of Tf of the TfR, also inhibits tumor growth.

Evidence that neoplastic cells are sensitive to Fe chelation comes from work in vitro in cell culture experiments, and in vivo in clinical trials where the chelator used to treat Fe overload, desferrioxamine (DFODFO), and other Fe chelators effectively inhibit proliferation. One of the most significant reports demonstrating a pronounced therapeutic effect of DFO comes from a study done in patents with neuroblastoma (NB). In this latter trial, DFO given as an 8 hr intravenous infusion resulted in 7 of 9 patients having more than a 50% decrease in bone infiltration of tumor cells. Moreover, in 1 patient, a 48% decrease in tumor size was reported. In more recent investigations, DFO was combined with cytotoxic agents (cyclophosphamide, etoposide, thio-TEPA and carboplatin) in patients with stage III and IV NB. From 57 patients studied, there were 24 complete responses, 5 very good partial responses, 21 partial responses, 3 minor responses and 4 with progressive disease.

It has now been ascertained that DFO, which is now the drug in current clinical use, is very expensive, orally ineffective and requires long subcutaneous infusion (12–24 hr/day, 5–7 days/week) to effect significant Fe mobilization (Olivieri et al., 1997, Blood 89 739–61; Richardson et al., 1998, Am. J. Hematol. 58 299–305). The need for an orally effective and economical Fe chelator has recently been emphasized by the failure of deferiprone (also known as L1 or 1,2-dimethyl-3-hydroxypyrid-4-one) to successfully chelate Fe from Fe-overloaded patients (Olivieri et al., 1988, New Eng. J. Med. 337 417–23). In fact, treatment of patients with this later drug resulted in hepatic fibrosis and an increase in liver Fe levels.

One important group of chelators that have shown high Fe chelation efficacy both in vitro and in vivo are those ligands of the pyridoxal isonicotinoyl hydrazone (PIH) class referred to in Richardson et al., 1998, supra. These chelators have a very high affinity and specificity for Fe(III) that is similar to that found for DFO and much greater than that of ethylenediaminetetracetic acid (EDTA) as reported in Richardson et al., 1989, supra and Vitolo et al., 1990, Inorg. Chim. Acta 733 39–50. In addition, these ligands are synthesized by a simple one-step Schiff base condensation, are economical and orally effective as discussed in Richardson et al., 1989, J. Lab Clin. Med. 131 306–15. Interestingly, PIH can chelate Fe from the mitochondrion, a site that may become loaded with Fe in the neurodegenerative disease Friedreich's ataxia (Babcock et al., 1997, Science 276 1709–12; Foury et al., 1997, FEBS Lett. 411 373–7; Rotig et al., 1997, Nature Genetics 12 215–7).

Previous studies have characterized the biological and chemical properties of analogues of PIH, some of which show higher activity on a molar basis than the parent compound itself. These compounds were derived from three groups of aromatic aldehydes, namely, pyridoxal, salicylaldehyde and 2-hydroxyl-1-naphthylaldehyde. Generally, chelators derived from pyridoxal were shown to possess high chelation efficacy but low anti-proliferative activity, while ligands derived from 2-hydroxy-1-naphthylaldehyde had high Fe chelation efficacy and potent anti-proliferative activity. Hence, aroylhydrazones derived from pyridoxal were considered to be possibly useful as agents to treat Fe overload disease while chelators derived from 2-hydroxyl-1-naphthylaldehyde were considered to have better potential for the treatment of cancer. It should be noted that many other Fe chelators have also demonstrated anti-proliferative activity, including DFO. In fact, some of the most potent effects of DFO have been reported when this drug was used against the pediatric tumor neuroblastoma. In Cory et al., 1995, Adv. Enzyme Regul. 35 55–68 and Liu et al., 1995, Prog. Med. Chem. 32 1–35, there are disclosed a closely related group of chelators derived from 2-pyridylcarboxaldehyde and thiosemicarbazide (e.g. 3-aminopyridine-2-carboxaldehyde thiosemicarbazone) which were found to be among the most effective inhibitors of ribonucleotide reductase yet identified. However, these chelators, while having high anti-proliferative properties, were found to have only moderate chelation efficacy and moderate lipophilicity which made such chelators less efficient in regard to treatment of Fe overload diseases.

Friedreich's ataxia (FA) is a severe neurodegenerative condition. In 97% of patients the disease is due to a GAA triplet repeat expansion in intron 1 of the FRDA gene resulting in a marked decrease in its expression. The protein encoded by this gene is known as frataxin and is found within the mitochondrion. Over the last few years evidence has accumulated to suggest that frataxin plays a role in mitochondrial Fe metabolism. Studies using the yeast cell showed that deletion of the homologous gene (YFH1), resulted in an accumulation of mitochondrial Fe resulting in the loss of mitochondrial DNA, [Fe-S] cluster-containing enzymes, and respiration. Like the human FRDA gene, YFH1 encodes a mitochondrial protein (Yfh1p). When YFH1 was reintroduced back into the yeast, mitochondrial Fe was exported back out into the cytosol, suggesting a "mitochondrial Fe cycle".

Consistent with the knockout yeast model, it was noted that reductions in mitochondrial DNA, complex I, complex II/III, and aconitase occurred in the heart of FA patients, observations consistent with mitochondrial damage. In addition, it was reported increased Fe deposition in the heart, liver, and spleen was reported in FA patients in a pattern consistent with a mitochondrial location. This work suggesting the pathology of FA in humans is caused by mitochondrial Fe overload was strongly supported by work showing Fe deposits within the heart myofibrils, defective myocardial and skeletal muscle mitochondrial respiration, and perturbations in the heme biosynthesis pathway.

Since the pathology of FA is linked to mitochondrial Fe overload, new therapies based on these results could provide hope for FA patients. One strategy is the use of specific Fe chelators that can permeate the mitochondrion. Already a trial supported by the National Institute of Health is investigating the use of the clinically used Fe chelator desferrioxamine (DFO) to treat FA patients. However, DFO cannot efficiently mobilize Fe from cells, and previous studies have demonstrated that it is not effective at mobilizing Fe from Fe-loaded mitochondria in reticulocytes.

In contrast to DFO, another chelator known as pyridoxal isonicotinoyl hydrazone (PIH) shows high activity at mobilising Fe from an experimental model of mitochondrial Fe overload in reticulocytes. A variety of studies, in vitro, in vivo, and a clinical trial, have demonstrated that PIH and its analogues show potential for the treatment of Fe-overload disease.

Although a lot of work has been done to develop Fe chelators for use in medical applications, there is still a need for new chelators which have safe and efficacious characteristics. The present inventors have now developed new Fe chelators that have been found as suitable candidate for use in treating Fe overload disease. The present inventors have synthesized a new group of ligands known as 2-pyridylcarboxaldehyde isonicotinoyl hydrazone (PCIH) analogues. Several PCIH analogues are more active than DFO or PIH at mobilizing Fe from a neuroepithelioma cell line (SK-N-MC), and showed low anti-proliferative activity.

DISCLOSURE OF INVENTION

In a first aspect, the present invention provides 2-pyridylcarboxaldehyde isonicotinoyl hydrazone (PCIH) analogues suitable for use as in vivo iron chelators, the PCIH analogue having Formula I:

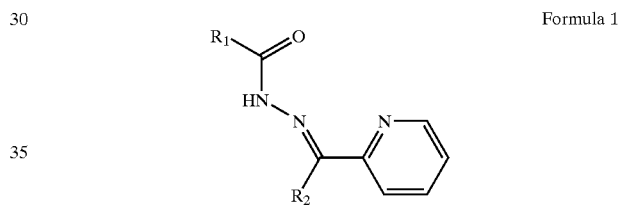

Formula 1 wherein R1 is an aromatic or heterocyclic group except unsubstituted pyridine and R2 is either H or OH; isomers thereof or salts thereof.

Preferably, R1 is a hydrophobic aromatic or heterocyclic group. More preferably, R1 is a phenyl, pyridine, furan or thiophene ring optionally with alkyl, halo, nitro, amine and hydroxyl attached to any of the vacant positions on the ring. More preferably, R1 is benzoyl, halogenated benzoyl, m-bromo benzoyl, isonicotinoyl, or thiophene group.

The present inventors have found that when R1 is hydrophilic in nature, the analogue is more water soluble, but the chelator exhibits poor efficacy at mobilizing Fe. As a variety of analogues with different R1 groups have been produced, the invention includes a range of analogues with different R1 groups.

More preferably, the analogue is selected from 2-pyridylcarboxaldehyde m-bromobenzoyl hydrazone (PCBBH), 2-pyridylcarboxaldehyde 2-thiophenecarboxyl hydrazone (PCTH).

The Br substituent of the 2-pyridylcarboxaldehyde m-bromobenzoyl hydrazone (PCBBH) may be substituted with any other halide group.

In a second aspect, the present invention provides a pharmaceutical composition suitable for use as an in vivo chelator, the composition comprising a therapeutically effective amount of an 2-pyridylcarboxaldehyde isonicotinoyl hydrazone (PCIH) analogue having Formula 1 together with a pharmaceutically suitable carrier or diluent, wherein

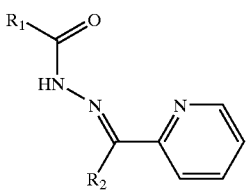

Formula 1 wherein R1 is an aromatic or heterocyclic and R2 is either H or OH; isomers thereof or salts thereof.

Preferably, R1 is a hydrophobic aromatic or heterocyclic group. More preferably, R1 is a phenyl, pyridine, furan or thiophene ring optionally with alkyl, halo, nitro, amine or hydroxyl attached to any of the vacant positions on the ring. In one preferred form, R1 is benzoyl, halogenated benzoyl, m-bromo benzoyl, isonicotinoyl, or thiophene group.

Preferably the analogue is selected from the compounds 2-pyridylcarboxaldehyde isonicotinoyl hydrazone (PCIH), 2-pyridylcarboxaldehyde 2-thiophenecarboxyl hydrazone (PCTH), -pyridylcarboxaldehyde benzoyl hydrazone (PCBH), 2-pyridylcarboxaldehyde m-bromobenzoyl hydrazone (PCBBH).

The Br substituent of the 2-pyridylcarboxaldehyde m-bromobenzoyl hydrazone (PCBBH) may be substituted with any other halide group.

In one embodiment, the carrier is an orally administrable carrier. Preferably, the pharmaceutical composition is in a dosage form formulated as enterically coated, granules or capsules.

Preferably, the pharmaceutical composition further includes a suitable buffer to adjust the pH of the stomach of the patient or subject to a level that will minimize acid hydrolysis. Such a pH should be about 6–8 (more preferably about 7) for the active compounds per se inclusive of free bases and hydrochloride salts. More preferably the buffer is a phosphate-citrate buffer.

The language "administering a therapeutically effective amount" is intended to include methods of giving or applying an analogue to an organism which allow the analogue to perform its intended therapeutic function. The therapeutically effective amounts of the analogue will vary according to factors such as the type of disease of the individual, the age, sex, and weight of, and the ability of the analogue to chelate iron in cells of the individual. Dosage regima can be adjusted to provide the optimum therapeutic response. For example, several divided doses can be administered daily or the dose can be proportionally reduced as indicated by the exigencies of the therapeutic situation.

The analogue can be administered in a convenient manner such as by injection (subcutaneous, intravenous, etc.), oral administration, inhalation, transdermal application, or rectal administration. Depending on the route of administration, the analogue can be coated with a material to protect the analogue from the action of enzymes, acids and other natural conditions which may inactivate the analogue chelator.

The analogue can also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In these cases, the compositions must be sterile and must be fluid to the extent that easy syringability exits. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for examples, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the analogue in the required amount in an appropriate solvent with one or a combination of ingredients enumerated above, as required, followed by filtered sterilization. Generally, dispersions are prepared by incorporating the analogue into a sterile vehicle which contains a basic dispersion medium and the required other ingredients from those enumerated above.

The analogue can be orally administered, for example, with an inert diluent or an assimilable edible carrier. The analogue and other ingredients can also be enclosed in a hard or soft shell gelatin capsule, compressed into tablets, or incorporated directly into the individual's diet. For oral therapeutic administration, the analogue can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5 to about 80% of the weight of the unit. The amount of analogue in such therapeutically useful compositions is such that a suitable dosage will be obtained.

The tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the analogue can be incorporated into sustained-release preparations and formulations.

The language "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the analogue, use thereof in the therapeutic compositions and methods of treatment is contemplated. Supplementary active compounds can also be incorporated into the compositions according to the present invention. It is especially advantageous to formulate parenteral compositions in dosage unit form for ease of administration and uniformity of dosage. Dosage unit form as used herein refers to physically discrete units suited as unitary dosages for the individual to be treated: each unit containing a predetermined quantity of analogue is calculated to produce the desired therapeutic effect in association with the required pharmaceutical carrier. The specification for the novel dosage unit forms of the invention are dictated by and directly dependent on (a) the unique characteristics of the analogue and the particular therapeutic effect to be achieve, and (b) the limitations inherent in the art of compounding such an analogue for the treatment of iron-related or iron overload diseases in individuals. The principal analogue is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

Preferably the pharmaceutical composition is administered in a dosage regimen of 30–500 mg per kg of body weight of a patient. More preferably, the dosage regimen is 50–100 mg per kg of body weight.

In a third aspect the present invention provides a method of iron chelation therapy comprising administering to a patient a pharmaceutical composition according to the second aspect of the present invention.

In a fourth aspect, the present invention provides a method of treating an iron-overload disease in a subject, the method comprising administering to a subject a pharmaceutical composition according to the second aspect of the present invention.

In one embodiment, the iron-overload disease is β-thalassemia. In an alternate embodiment, the disease is Friedreich's ataxia.

In a fifth aspect, the present invention provide use of a 2-pyridylcarboxaldehyde isonicotinoyl hydrazone (PCIH) analogue according to the first or second aspects of the present invention in the manufacture of a medicament for the treatment of an iron-overload disease.

Considering the high potential of the PIH class of ligands which have high Fe chelation efficiency both in vivo and in vitro, the present inventors have synthesized a number or aroylhydrazones so as to identify Fe chelators more efficient than desferrioxamine (DFO) and more soluble than those of the PIH class. These compounds belong to a new series of tridentate chelators known as the 2-pyridylcarboxaldehyde isonicotinoyl hydrazone (PCIH) analogues. The Fe chelation efficacy and anti-proliferative activity of these chelators have been studied including their effects on the expression of genes (WAF1 and GADD45) known to be important in mediating cell cycle arrest at $G_1/S$. From chelators synthesized, three analogues, namely 2-pyridylcarboxaldehyde benzoyl hydrazone (PCBH), 2-pyridylcarboxaldehyde m-bromobenzoyl hydrazone (PCBBH), and 2-pyridylcarboxaldehyde 2-thiophenecarboxyl hydrazone (PCTH), showed greater Fe chelation activity than PIH. These ligands were highly effective at both mobilizing $^{59}Fe$ from cells and preventing $^{59}Fe$ uptake from $^{59}Fe$-transferrin and caused a marked increase in the RNA-binding activity of the iron-regulatory proteins (IRPs). In comparison to the cytotoxic Fe chelator, 2-hydroxy-1-naphthylaldehyde isonicotinoyl hydrazone (311), these ligands have far less effect on cellular growth and $^3H$-thymidine, $^3H$-leucine or $^3H$-uridine incorporation. In addition, in contrast to 311 that markedly increased WAF1 and GADD45 mRNA expression. PCBH and PCTH did not have any effect, while PCBBH increased the expression of GADD45 mRNA. Collectively, the present results demonstrate the potential of several of these ligands as agents for the treatment of Fe overload disease.

Of these particular compounds, it has now been found that PCTH, PCBH and PCBBH have the potential for use as agents for treatment of Fe overload.

The compositions should also, if desired, contain a suitable buffer to adjust the pH of the stomach of the patient or subject to a level that will minimize acid hydrolysis. Such a pH should be about 6–8 (more preferably about 7) for the active compounds per se inclusive of the free bases and hydrochloride salts discussed hereinafter.

Such buffers are well known to include single or multiple components such as those listed in the UA Pharmacopoeia XXII, specifically for example, ammonium, potassium and/or sodium salts of phosphoric acid, in conjunction with citric acid. Use of a pharmaceutically acceptable antacid, such as aluminum and/or magnesium hydroxide or calcium carbonate or glycine USP/NF sufficient to neutralize the normally present 0.1 M HCl in the 200–600 ml of stomach fluids (20 to 60 meq of base). A specific example of phosphate-citrate buffer, pH 6.8, would result from 9.1 ml of 0.1 M citric acid combined with 40.9 ml 0.2M dibasic sodium phosphate solutions.

Measurement of the bioefficiency of chelators of the invention can be carried out in accordance with the methods described in Brittenham, 2 Apr. 1990. Seminar in Haematology 27 112–116 or as described in U.S. Pat. No. 5,834,492 which is incorporated herein by reference.

The active compounds of the invention may be made into an enteric coated granule formulation using the formulations described in U.S. Pat. No. 5,834,492. For Example, the drug is combined with sufficient ethanol to make it into a slightly damp thick paste which is further mixed with providone and mechanically applied as a layered coating over a spherical support of defined mesh size. The supports themselves, if desired, are usually pharmacologically inactive, but an active support may also be utilized. The spherical matrix could be an acid resistant, biocompatible polymer. Examples are polycarbonate, polyethylene, teflon, microcrystalline cellulose, or other plastics. Other biocompatible polymers can also be used.

Enteric polymers and plasticizers are combined in ethanol to form a solution which is carefully sprayed over the support as a film which covers the active drug and protects it from premature dissolution in an environmental pH which is unfavourable for best absorption. The ensuing product is mechanically dried while preserving the uniformity of the enteric coating.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any description of prior art documents herein is not an admission that the documents form part of the common general knowledge of the relevant art in Australia.

In order that the present invention may be more clearly understood preferred forms will be described with reference to the following examples and drawings.

MODES FOR CARRYING OUT THE INVENTION

EXPERIMENTAL

Figure 1:
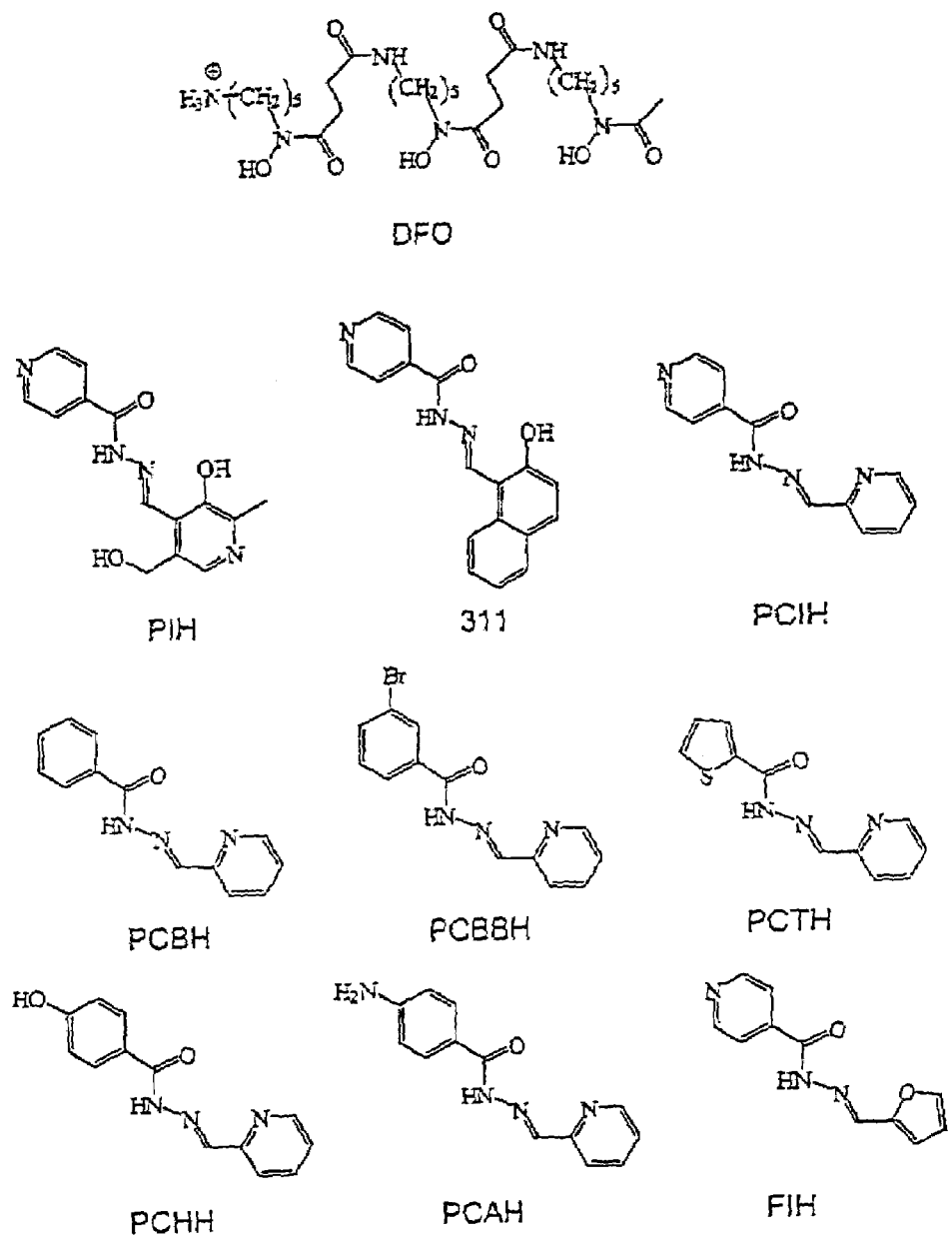
FIG. 1. The structures of the iron chelators assessed in this study: desferrioxamine (DFO), pyridoxal isonicotinoyl hydrazone (PIH), 2-hydroxy-1-naphthylaldehyde isonicotinoyl hydrazone (311), 2-pyridylcarboxaldheyde isonicotinoyl hydrazone (PCIH), 2-pyridylcarboxaldehyde benzoyl hydrazone (PCBH), 2-pyridylcarboxaldehyde m-bromobenzoyl hydrazone (PCBBH), 2-pyridylcarboxaldehyde thiophenecarboxyl hydrazone (PCTH), 2-pyridylcarboxaldehyde p-hydroxybenzoyl hydrazone (PCHH), 2-pyridylcarboxaldehyde p-aminobenzoyl hydrazone (PCAH), 2furoylcarboxaldehyde isonicotinoyl hydrazone (FIH).

Synthesis of Iron Chelators and Their Preparation for Screening in Culture

PCIH analogues according to the present invention were synthesized by Schiff base condensation between 2-pyridinecarboxaldehyde and the respective acid hydrazides. The chelators were characterized by a combination of elemental analysis, infrared spectroscopy. $^1$H-NMR spectroscopy and X-ray crystallography. Both PIH and the PIH analogue 2-hydroxy-1-naphthylaldehyde isonicotinoyl hydrazone (311) were synthesized and characterized as described previously in Richardson et al., 1995. Desferrioxamine (desferrioxamine mesylate: DFO) was purchased from Ciba-Geigy Pharmaceutical Co., Summit, N.J. All of the aroylhydrazone chelators were dissolved in dimethyl sulphoxide (DMSO) as 10 mM stock solutions immediately prior to an experiment and then diluted in 10% fetal calf serum (FCS: Commonwealth Serum Laboratories, Melbourne, Australia) so that the final concentration of DMSO was equal to or less than 0.5% (v/v). After dilution, the solutions were mixed vigorously to ensure total solubilization. Previous studies by the inventors have demonstrated that DMSO at this concentration has no effect on either cellular proliferation. $^{59}$Fe release from prelabelled cells, or the ability of the cells to remove $^{59}$Fe from Tf (Richardson et al., 1995).

Synthesis of Free Bases

All chelators were prepared by refluxing 10 mmol of the acid hydrazide with 2-pyridine carboxaldehyde (or 2-furfural with isonicotinine acid hydrazide for FIH) in 50% aqueous ethanol (40 mL) for 30 min. After cooling, the product was collected by filtration, washed with diethyl ether and dried in a vacuum desiccator. Yields were typically 70–80%.

Synthesis of the Hydrochloride Salts

A sample (0.25 g) of each free base was dissolved in ethanol (15 mL). Concentrated hydrochloric acid (1 mL) was added with stirring followed by diethyl ether (40 mL) to afford precipitation of the hydrochloride salt. The compound was filtered off and dried in a vacuum desiccator."

Cell Culture

The human SK-N-MC neuroepithelioma and SK-Mel-28 melanoma cell lines were from the American Type Culture Collection (ATCC), Rockville, Md., USA. The SK-N-MC cell line was originally classified as a neuroblastoma, but has been recently reclassified as a neuroepithelioma, a closely related neuroectodermal malignancy. The BE-2 neuroblastoma cell line was a kind gift from Dr Greg Anderson, Queensland Institute of Medical Research, Queensland. The SK-N-MC and SK-Mel-28 cell lines were grown in Eagle's modified minimum essential medium (MEM: Gibco BRL, Sydney, Australia) containing 10% FCS, 1% (v/v) non-essential amino acids (Gibco), 2 mM L-glutamine (Sigma Chemical Co., St. Louis, Mo., USA) 10 $\mu$g/ml of streptomycin (Gibco). 100 U/ml penicillin (Gibco) and 0.28 $\mu$g/ml of fungizone (Squibb Pharmaceuticals, Montreal, Canada). This growth medium will be subsequently referred to as a complete medium. The BE-2 cell line was grown in Rosewall Park Memorial Institute (RPMI) medium with all of the supplements described above for MEM. Cells were grown in an incubator (Forma Scientific, OH, USA) at 37° C. in a humidified atmosphere of 5% $CO_2$/95% air and subcultured as described previously (Richardson et al., 1990, Biochim. Biophys. Acta 1053 1–12). Cellular growth and viability were monitored using phase-constant microscopy and trypan blue staining.

Effect of Chelators on Cellular Proliferation

The effects of the chelators on the proliferation of SK-N-MC neuroepithelioma cells were examined using the MTT (3-(4,5-dimethylthiazol-2-yl)-2,5-diphenyltetrazolium) assay by essentially the same method as described previously (Richardson et al., 1995). Cellular proliferation was examined by seeding cells in 96-well microtitre plates at 15,000 cells/well in 0.1 mL of complete medium containing human diferric Tf (1.25 $\mu$M). This seeding density resulted in exponential growth of the cells throughout of the assay. The cells were allowed to grow overnight and the chelators were then added in 0.1 mL of complete medium containing diferric transferrin (1.25 $\mu$M). The final concentrations of the chelators were 0.39–50 $\mu$M. Control samples contained complete medium and diferric Tf (1.25 $\mu$M). Cells were incubated with the chelators for 90 hrs at 37° C. in a humidified atmosphere containing 95% air and 5% $CO_2$. After this incubation, 0.01 mL of MTT was added to each well and the plates incubated for 2 hrs at 37° C. The cells were solubilized by adding 0.1 mL of 10% SDS-50% isobutanol in 0.01 M HCl and the plates were read at 570 nm on a scanning multiwell spectrophotometer (Titertek Multiscan; Beckman Instruments Inc., California). As shown previously for the SK-N-MC cell line, MTT colour formation was directly proportional to the number of viable cells (Richardson et al., 1995). The results of the MTT assays are expressed as a percentage of the control value.

Preparation of $^{59}$Fe-Transferrin

Apotransferrin (Sigma Chemical CO., St. Louis, U.S.A.) was prepared and labelled with $^{59}$Fe (as ferric chloride in 0.1 M HCl, Dupont NEN, MA, U.S.A.) to produce $^{59}$Fe-transferrin ($^{59}$Fe-Tf) using standard procedures described previously (Richardson et al., 1990). The saturation of Tf with Fe was monitored by uv-vis spectrophotometry using the absorbance at 280 nm (protein) compared with that at 456 nm (Fe-binding site). In all experiments, fully saturated diferric Tf was used.

Effect of the Chelators on $^3$H-Thymidine, $^3$H-Leucine and $^3$H-Uridine Incorporation Labelling of cells with $^3$H-thymidine (20 Ci/mmol: Dupont NEN, MA, U.S.A.), $^3$H-uridine (42.7 Ci/mmol/ Dupont NEN, MA, U.S.A.) and $^3$H-leucine (52 Ci/mmol: Dupont NEN) was estimated after precipitation with trichloroacetic acid (TCA). After a 20 hr incubation with the chelators, $^3$H-leucine, $^3$H-uridine or $^3$H-thymidine (1 $\mu$Ci/ ml) were then added for 2 hrs at 37° C. Subsequently, petri dishes containing cell cultures were placed on ice and washed four times with ice-cold Hanks' balanced salt solution (BSS) and the cells detached from the plate using 1 mM EDTA in Ca/Mg-free saline. The cells were then pelleted by centrifugation, the supernatant removed and the pellet frozen at –70° C. After thawing the cells on ice, 1 ml of ice-cold 20% TCA was added and the solution then vortexed and kept on ice for 1 hr with periodic mixing. This solution was then centrifuged at 15,000 rpm for 15 mins at 4° C. and the supernatant removed. The pellet was then washed twice with 1 ml of ice-cold 10% TCA. The pellet was dissolved in 0.5 ml of 1 M NaOH and transferred to scintillation tubes with 3 ml of scintillant. Radioactivity was measured on a β-scintillation counter (LKB Wallace, Finland).

Iron Uptake and Iron Efflux Experiments

The effect of chelators on $^{59}$Fe uptake from $^{59}$Fe-Tf and $^{59}$Fe release from prelabelled cells was studied using standard procedures reported previously (Richardson et al., 1994, J. Lab Clin. Med. 124 660–71). The amount of $^{59}$Fe internalized by the cells was measured by incubation with the general protease pronase (1 mg/ml) for 30 min at 4° C. to remove membrane-bound $^{59}$Fe and Tf (Richardson et al., 1990; Baker et al., 1998, Biochim. Biophys. Acta 1380 21–30). Control experiments reported in previous studies have found that this technique is valid for estimation of $^{59}$Fe internalization of cells (Richardson et al., 1990; Baker et al., 1998).

Iron Regulatory Protein Gel-Retardation Assay

A gel-retardation assay was used to measure the interaction between the IRPs and IRE using established techniques (Leibold et al., 1998. Proc. Natl. Acad. Sci. USA 85 2171–5; Müllner et al., 1989 Cell 58 373–82). Briefly, after incubation with medium alone (control) or medium containing ferric ammonium citrate (100 $\mu$g/ml: Aldrich Ltd., Sydney, Australia) or the chelator. $2-5\times10^a$ cells were washed with ice-cold phosphate-buffered saline (PBS) and lysed at 4° C. in 40 $\mu$l of ice-cold Munro extraction buffer (10 mM HEPES, pH 7.6, 3 mM $MgCl_2$, 40 mM KCl, 5% glycerol, 1 MM dithiothreitol and 0.5% Nonidet P-40). After lysis, the samples were then centrifuged at 10,000 rpm for 3 mins at 4° C. to remove nuclei and the supernatant stored at –70° C. Frozen cytoplasmic extracts were thawed on ice and then centrifuged at 15,000 rpm for 10 min at 4° C. The protein concentration of the soluble supernatant was determined using the BioRad protein assay (BioRad Ltd., USA).

Samples of cytoplasmic extracts were diluted to a protein concentration of 100 μg/ml in Munro buffer without Nonidet P-40 and 1 μg aliquots were analyzed for IRP by incubation with 0.1 ng (approximately $1 \times 10^5$ cpm) of $^{32}$P-labelled pGL66 RNA transcript (Leibold et al., 1988). The riboprobe was transcribed in vitro from linearized plasmid templates using SP6 RNA polymerase in the presence of $\alpha$-$^{32}$P UTP (Dupont, NEN). This latter reaction was performed using the Promega Riboprobe In Vitro Transcription Kit (Promega, Madison, Wis., USA). The probe was subsequently purified on a 6% urea/PAGE gel. To form RNA-protein complexes, cytoplasmic extracts containing 1 μg of protein were incubated for 10 mins at room temperature with the $^{32}$P-labelled riboprobe. Unprotected probe was degraded by incubation with 1 U of RNAse T1 for 10 mins at room temperature. Heparin (Sigma) at a final concentration of 5 mg/ml was then added and incubated with the extract for another 10 min at room temperature to exclude non-specific binding. RNA-protein complexes were analyzed in 6% non-denaturing polyacrylamide gels at 4° C. as described by Konarska et al., 1986, Cell 46 845–55. Gels were dried, covered in plastic film and exposed to Kodak XAR films at −70° C. with an intensifying screen.

Northern Blot Analysis

Northern blot analysis was performed by isolating total RNA using the Total RNA isolation Reagent from Advanced Biotechnologies Ltd (Surrey, United Kingdom). The RNA (15 μg) was heat denatured at 90° C. for 2 mins in RNA-loading buffer and then loaded onto a 1.2% agarose-formaldehyde gel. After electrophoresis, RNA was transferred to a nylon membrane (GeneScreen, New England Nuclear, Boston, USA) in 10xSSC using the capillary blotting method. The RNA was then cross-linked to the membrane using a UV-crosslinker (UV Stratalinker 1800, Stragene Ltd., USA).

The membranes were hybridized with probes specific for human WAF1, GADD-45 and β-actin. The WAF1 probe consisted of a 1 kb fragment from pSXV(ATTC: Cat. No. 79928). The GADD45 probe consisted of a 760 bp fragment from human GADD45 cDNA cloned into pHu145B2 (kindly supplied by Dr. Albert Fornace, National Cancer Institute, NIH, Maryland). The β-actin probe consisted of a 1.4 kb fragment from human β-actin cDNA cloned into pBluescript SK-(ATTC: at. No 37997).

Hybridization of probes to the membranes and their subsequent washing were performed as described by Mahmoudi and Lin, 1989, Biotechniques 7, 331–2 using a Hybaid Shake and Stack Hybridization oven (Hybaid Ltd., Middlesex, UK). The membranes were then exposed to Kodak XAR Films at −70° C. with an intensifying screen. The probes were stripped from the nylon membrane by boiling in a solution containing 10 mM Tris-HCl (pH 7.0). 1 mM EDTA (pH 8.0) and 1% SDS for 15–30 mins as described by the membrane manufacturer. Densitometric data were collected with a Laser Densitometer and analyzed by Kodak Biomax Software (Kodak Ltd, USA).

Reticulocytes

Reticulocytosis was induced by standard procedures (Richardson, D. R., Ponka, P and Vyoral, D (1996) Blood 87, 3477–3488) in New Zealand white rabbits by repeated phlebotomy by cardiac puncture using a protocol approved by the McGill University Animal Care Committee. Reticulocytes were identified based on staining with new methylene blue, and cell counts were determined using an improved Neubauer counting chamber.

Labelling of Transferrin

Apotransferrin (Sigma Chemical Co) was prepared and labelled with $^{59}$Fe (as ferric.chloride in 0.1 M HCl, Dupont NEN, MA, USA) to produce $^{59}$Fe$_2$-transferrin ($^{59}$Fe-Tf) using established methods (Richardson, D. R. and Baker, E. (1992) J Biol Chem. 267, 13972–13979).

Mobilisation of $^{59}$Fe from $^{59}$Fe-Loaded Reticulocytes

The $^{59}$Fe-labelled rabbit reticulocyte has been shown to be a useful model to investigate the ability of an Fe chelator to permeate the cell membrane and chelate intracellular Fe pools. Reticulocytes were obtained from chronically bled rabbits as described above and were incubated with 1 mM succinylacetone (SA: Sigma) to inhibit heme synthesis. After a 15 min preincubation in the presence of SA, $^{59}$Fe-Tf (3.75 mM) was added and incubated with the cells for 1 H at 37° C. with shaking. After this incubation the reticulocytes were washed three times with ice-cold PBS to remove non-specifically bound $^{59}$Fe-Tf. The washed $^{59}$Fe-labelled reticulocytes (30–35 μL) were incubated in buffered salt solution (250 μL final volume) with the apochelators. The SA was present in all incubations with the chelators to prevent the utilization of non-heme $^{59}$Fe for heme synthesis. After the incubation, $^{59}$Fe was measured both in washed reticulocytes and in the medium, and the percentage of $^{59}$Fe mobilized from the reticulocytes was then calculated.

In some experiments, washed $^{59}$Fe-labelled reticulocytes were lysed with 200 μL of ice-cold distilled water and the proteins precipitated with 1 ml ice-cold 95% ethanol. The mixture was then centrifuged (13,000 rpm/30 min/4° C.) on a IEC Micromax microcentrifuge (IEC, Canada) to result in an ethanol-soluble fraction containing $^{59}$Fe-bound to low $M_r$ chelators, and an ethanol-precipitated fraction containing protein-bound $^{59}$Fe. Previous studies have demonstrated that this method results in the precipitation of $^{59}$Fe in ferritin and transferrin while $^{59}$Fe bound to chelators remains in a soluble form. An increase of $^{59}$Fe in the alcohol-soluble fraction shows that the chelator can cross the cell membrane and form intracellular Fe complexes which are released with limited efficiency.

RESULTS

Production of 2-Pyridylcarboxaldehyde Isonicotinoyl Hydrazone (PCIH) Analogues

PCIH-H$_2$O: Anal. Calcd for $C_{12}H_{12}N_4O_2$: C, 59.0; H, 5.0; N. 22.9. Found: C, 59.2; H, 4.9; N, 22.9%. $^1$H NMR (MeOH-d$_4$) δ (ppm vs TMS) 7.44 (m, 1H); 7.90 (m, 3H); 8.26 (d, 1H); 8.41 (s, 1H); 8.57 (d, 1H); 8.74 (dd, 2H).

PCBH-H$_2$O: Anal. Calcd for $C_{13}H_{12}N_3O_2$: C, 64.2; H, 5.4; N. 17.3. Found: C, 64.1; H, 5.4; N, 17.3%. $^1$H NMR (MeOH-d$_4$) δ (ppm vs TMS) 7.41 (m, 1H); 7.51 (m, 3H); 7.92 (d, 1H); 7.95 (m, 2H); 8.28 (d, 1H); 8.39 (s, 1H); 8.55 (d, 1H).

PCBBH-H$_2$O: Anal. Calcd for $C_{13}H_{12}BrN_3O_2$: C, 48.5; H, 3.8; N. 13.0. Found: C, 47.8; H, 3.6; N, 12.7%. $^1$H NMR (MeOH-d$_4$) δ (ppm vs TMS) 7.44 (m, 2H); 7.76 (d, 1H); 7.91 (m, 2H); 8.12 (s, 1H); 8.27 (d, 1H); 8.39 (s, 1H); 8.55 (d, 1H).

PCTH: Anal. Calcd for $C_{11}H_9N_3OS$: C, 57.1; H, 3.9; N. 18.2. Found: C, 57.2; H, 4.0; N, 17.3%. $^1$H NMR (MeOH-d$_4$) δ (ppm vs TMS) 7.20 (m, 1H); 7.43 (m, 1H); 7.85 (m, 3H); 8.26 (d, 1H); 8.37 (s, 1H); 8.56 (d, 1H).

PCHH-H$_2$O: Anal. Calcd for $C_{12}H_{11.5}N_3O_{2.25}$: C, 63.8; H, 4.3; N. 17.2. Found: C, 63.6; H, 4.8; N, 16.4%. $^1$H NMR (MeOH-d$_4$) δ (ppm vs TMS) 6.88 (dd, 2H); 7.43 (m, 1H); 7.86 (m, 3H); 8.29 (d, 1H); 8.36 (s, 1H); 8.55 (d, 1H).

PCAH-H$_2$O: Anal. Calcd for C$_{13}$H$_{14}$N$_4$O$_2$: C, 60.5; H, 5.5; N, 21.7. Found: C, 60.3; H, 5.5; N, 21.4%. $^1$H NMR (MeOH-d$_4$) δ (ppm vs TMS) 6.69 (dd, 2H); 7.39 (m, 1H); 7.74 (dd, 2H); 7.85 (td, 1H); 8.26 (d, 1H); 8.33 (s, 1H); 8.52 (d, 1H).

FIH: Anal. Calcd for C$_{11}$H$_9$N$_3$O$_2$: C, 61.4; H, 4.2; N. 19.5. Found: C, 61.6; H, 4.2; N, 19.4%. $^1$H NMR (MeOHd$_4$) (ppm vs TMS) δ 6.59 (dd, 1H); 7.00 (d, 1H); 7.69 (d, 1H); 7.86 (dd, 2H); 8.26 (s, 1H); 8.73 (dd, 2H).

PCIH-2HCl-2.5H$_2$O: Anal. Calcd for C$_{12}$H$_{17}$Cl$_2$N$_4$O$_{3.5}$: C, 41.9; H, 5.0; N. 16.3. Found: C, 41.6; H, 4.5; N, 16.0%. $^1$H NMR (D$_2$O), δ (ppm vs TMS): 8.17 (t, 1H), 8.40 (d, 1H), 8.59 (d, 2H), 8.70 (s, 1H), 8.75 (t, 1H), 8.94 (d, 1H), 9.12 (d, 2H).

PCBH-HCL-1.5H$_2$O: Anal. Calcd for C$_{13}$H$_{15}$ClN$_3$O$_{2.5}$: C, 54.1; H, 5.2; N. 14.6. Found: C, 53.9; H, 4.8; N, 14.1%. $^1$H NMR (D$_2$O), δ (ppm vs TMS): 7.39–7.53 (m, 3H), 7.80 (d, 2H), 7.97 (t, 1H), 8.12 (d, 1H), 8.32 (s, 1H), 8.55 (t, 1H), 8.69 (d, 1H).

PCBBH-HCl: Anal. Calcd for C$_{13}$H$_{11}$ClN$_3$O: C, 45.8; H, 3.3; N. 12.3. Found: C, 45.2; H, 4.1; N, 13.3%. $^1$H NMR (D$_2$O), δ (ppm vs TMS): 7.25 (m, 2H), 7.50 (d, 1H), 7.7–8.0 (m, 4H), 8.5 (s, 1H), 8.70 (d, 1H).

PCTH-HCl-H$_2$O: Anal. Calcd for C$_{11}$H$_{12}$ClN$_3$2S: C, 46.2; H, 4.2; N. 14.7. Found: C, 45.6; H, 4.1; N, 14.3%. $^1$H NMR (D$_2$O), δ (ppm vs TMS): 7.2 (m, 2H), 7.7–8.0 (m, 3H), 8.4–8.6 (m, 2H), 8.50 (d, 1H).

PCHH-HCl: Anal. Calcd for C$_{13}$H$_{16}$ClN$_3$O$_4$: C, 49.8; H, 5.1; N. 13.4. Found: C, 50.2; H, 4.9; N, 13.1%. $^1$H NMR (D$_2$O), δ (ppm vs TMS): 6.60 (d, 2H), 7.60 (d, 2H), 7.91 (t, 1H), 8.01 (s, 1H), 8.48 (t, 1H), 8.59 (d, 1H).

PCAH-HCl: Anal. Calcd for C$_{13}$H$_{16}$Cl$_2$N$_4$O$_2$: C, 44.7; H, 5.2; N. 16.0. Found: C, 44.7; H, 5.2; N, 15.9%. $^1$H NMR (D$_2$O), δ (ppm vs TMS): 7.28 (d, 2H), 7.90 (d, 2H), 8.20 (t, 1H), 8.40 (s, 1H), 8.60 (t, 1H), 8.80 (d, 1H).

FIH-2HCl-H$_2$O: Anal. Calcd for C$_{11}$H$_{13}$Cl$_2$N$_3$O$_3$: C, 49.0; H, 4.5; N. 15.6. Found: C, 49.2; H$_2$, 4.5; N, 15.6%. $^1$H NMR (D$_2$O), δ (ppm vs TMS): 6.64 (m, 1H), 7.01 (d, 1H), 7.71 (s, 1H), 8.26 (s, 1H), 8.42 (d, 2H), 8.99 (d, 2H).

The chelators in their free base form were sparingly soluble in water but are quite soluble in methanol and somewhat less so in ethanol. Upon protonation of their basic groups, the aqueous solubility of all chelators is dramatically increased. The hydrochloride salts of PCBBH-HCl and PCTH-HCl exhibit the lowest aqueous solubility of the series, whereas the most soluble chelators are PCIH-2HCl and PCAH-2HCl (both diprotic acids).

The $^1$H NMR spectra of the hydrochloride salts in water are quite similar to those of the corresponding free bases (in methanol). Most importantly, the imine singlet resonance is observed in all cases, which indicates that the imine functional group remains intact upon formation of the hydrochloride salt. Moreover, the protonated chelators do not exhibit any noticeable imine hydrolysis over a period of a week in aqueous solution as shown by NMR spectroscopy.

The degree of protonation was dependent on the number of basic groups present. The isonicotinoyl, p-aminophenyl and 2-pyridyl groups all underwent protonation. The imine N-atom (a potentially basic site) was not protonated unless the adjacent heterocycle was itself non-basic (i.e. the furyl group in FIH). Internal hydrogen bonding of the imine N-atom with the protonated pyridinium group appears to explain the resistance of the imine to protonation in these ligands.

Effect of the Chelators on Iron Release from Prelabelled Cells and Iron Uptake from Transferrin The ability of the PCIH analogues to increase $^{59}$Fe release from SK-N-MC cells was compared to "standard chelators" (DFO, PIH and 311) whose activity has been previously documented in this cell line. The efflux of $^{59}$Fe from SK-N-MC cells was examined after a 3 hr labelling period with $^{59}$Fe-Tf (0.75 μM) followed by a 3 hr reincubation in the presence and absence of DFO (100 μM) or the remainder of the ligands at 50 μM (FIG. 2A). It should be noted that DFO was screened at 100 μM in all experiments because of its low Fe chelation efficacy in SK-N-MC cells. Chelators 311, PIH, PCTH, PCBH and PCBBH showed similar activity resulting in the release of 40–42% of cellular $^{59}$Fe. The mobilization of $^{59}$Fe by PCIH was similar to that of DFO which released 19% of cellular $^{59}$Fe. In contrast, FIH, PCAH and PCHH did not appreciably increase $^{59}$Fe mobilization over that observed for the control medium (FIG. 2A).

To determine the ability of the chelators to inhibit $^{59}$Fe uptake from $^{59}$Fe-Tf (0.75 μM). SK-N-MC cells were incubated for 3 hrs at 37° C. with $^{59}$Fe- and either DFO (100 μM) or the other chelators (50 μM) (FIG. 2B). Ligands 311, PIH, PCTH, PCBH and PCBBH showed much greater efficacy than DFO at preventing $^{59}$Fe uptake from $^{59}$Fe-Tf (FIG. 2B), decreasing it to 13–30% of the control value respectively, whereas DFO reduced it to 91% of the control (FIG. 2B). In terms of the other chelators, PCIH was slightly more effective than DFO, while FIH, PCAH and PCHH had no effect on $^{59}$Fe uptake from $^{59}$Fe-Tf. Considering these data, in both $^{59}$Fe uptake and $^{59}$Fe efflux studies, three of the PCIH analogues, namely PCTH, PCBH and PCBBH, showed activity that was greater than DFO and comparable to PIH and 311 (FIGS. 2A and 2B).

To further investigate the efficacy of the most effective PCIH analogues identified from the screening studies above, the efficacy of PIH, PCIH, PCTH, PCBH and PCBBH at mobilizing $^{59}$Fe from SK-N-MC cells at a range of ligand concentrations was compared (0.5–50 μM; FIG. 3A). The mobilization of $^{59}$Fe from SK-N-MC cells was examined after a 3 hr labelling period with $^{59}$Fe-Tf (0.75 μM) followed by a 3 hr reincubation in the presence and absence of effective chelators (0.5–50 μM; FIG. 3A). The $^{59}$Fe release mediated by all chelators was biphasic as a function of chelator concentration, with $^{59}$Fe release beginning to plateau at a ligand concentration of 25 μM. It was apparent that at chelator concentrations up to 10 μM, the most effective chelators at mobilizing $^{59}$Fe were PCTH and PCBBH (FIG. 3A). However, as the ligand concentration was increased up to 25 and 50 μM, the activity of PCTH and PCBBH became similar to PIH and PCBH. PCIH was the least effective chelator at all concentrations (FIG. 3A).

Further studies examined the effect of chelator concentrations (0.5–50 μM) on the uptake of $^{59}$Fe from $^{59}$Fe-Tf (0.75 μM) during a 3 hr incubation (FIG. 3B). Similar to the results found in the efflux studies above. PCTH and PCBBH were the most effective chelators at preventing $^{59}$Fe uptake from $^{59}$Fe-Tf at ligand concentrations up to 10 μM, while at concentrations from 25–50 μM the activity of PIH, PCIH, PCTH and PCBH were similar (FIG. 3B). Again, PCIH was the least effective chelator at all concentrations examined. To determine if there were any differences in Fe chelation efficacy of the ligands between different cell types, the activity of the three most effective PCIH analogues (PCTH, PCBH and PCBBH) were compared to DFO and 311 in BE-2 neuroblastoma cells, SK-N-MC neuroepithelioma cells and SK-Mel-28 melanoma cells (Tables 1 and 2). Examining the ability of the chelators to mobilize $^{59}$Fe from cells prelabelled for 3 hrs with $^{59}$Fe-Tf (0.75 μM) and then reincubated for 3 hrs. DFO (100 μM) had comparable activity to 311 and the 3 PCIH analogues (50 μM) at mobilizing $^{59}$Fe from BE-2 cells (Table 1). In contrast, DFO was far less effective than either 311 or the PCIH analogues at mobilizing $^{59}$Fe from SK-N-MC or SK-Mel-28 Cells (Table 1).

Table 1. The effect of DFO, 311, PCTH, PCBH, or PCBHH on $^{59}$Fe release from BE-2 neuroblastoma cells, SK-N-MC neuroepithelioma cells, and SK-Mel-28 melanoma cells. Cells were labeled for 3 h at 37° C. with $^{59}$Fe-transferrin (0.75 μM), washed, and then reincubated with the chelators for 3 h at 37° C. The chelators 311, PCTH, PCBH, and PCBBH were screened at 50 μM while DFO was examined at 100 μM. Results are Mean±SD of three determinations in a typical experiment.

|          | % Cellular Iron Released |          |           |
| -------- | ------------------------ | -------- | --------- |
| Chelator | BE-2                     | SK-N-MC  | SK-Mel-28 |
| Control  | 9 ± 1                    | 5 ± 1    | 17 ± 2    |
| DFO      | 44 ± 2                   | 18 ± 3   | 27 ± 1    |
| 311      | 52 ± 1                   | 49 ± 1   | 70 ± 1    |
| PCTH     | 50 ± 1                   | 51 ± 5   | 57 ± 6    |
| PCBH     | 44 ± 1                   | 47 ± 3   | 54 ± 4    |
| PCBBH    | 48 ± 3                   | 47 ± 2   | 51 ± 5    |

Table 2. The effect of DFO, 311, PCTH, PCBH, or PCBHH on internalized $^{59}$Fe uptake from $^{59}$Fe-transferrin by BE-2 neuroblastoma cells, SK-N-MC neuroepithelioma cells, and SK-Mel-28 melanoma cells. Cells were incubated with the chelators and $^{59}$Fe-transferrin (0.75 μM) for 3 h at 37° C., washed, and incubated for 30 min at 4° C. with pronase (1 mg/ml) to separate the internalized from the membrane-bound $^{59}$Fe. All chelators were screened at a concentration of 50 μM except for DFO which was examined at 100 μM. Results are mean±SD (three determinations) from a typical experiment.

|          | Internalised Iron Uptake (% Control) |          |           |
| -------- | ------------------------------------ | -------- | --------- |
| Chelator | BE-2                                 | SK-N-MC  | SK-Mel-28 |
| Control  | 100 ± 9                              | 100 ± 8  | 100 ± 10  |
| DFO      | 42 ± 3                               | 100 ± 6  | 98 ± 7    |
| 311      | 8 ± 1                                | 10 ± 4   | 9 ± 1     |
| PCTH     | 25 ± 3                               | 16 ± 1   | 38 ± 6    |
| PCBH     | 25 ± 4                               | 20 ± 2   | 36 ± 6    |
| PCBBH    | 16 ± 1                               | 15 ± 2   | 54 ± 1    |

The effect of the chelators of preventing $^{59}$Fe uptake from $^{59}$Fe-Tf (0.75 μM) after a 3 hr incubation was also examined in the same cell lines (Table 2). The most effective chelator at inhibiting $^{59}$Fe uptake from $^{59}$Fe-Tf was 311, which reduced $^{59}$Fe uptake similarly in all 3 cell lines to 8–10% of the control value. The three PCIH analogues showed less activity than 311 but were far more effective than DFO (Table 2). It is of interest to note that DFO had little effect at inhibiting $^{59}$Fe uptake in both SK-N-MC neuroepithelioma cells and SK-Mel-28 melanoma cells (100 and 98% of the control, respectively), whereas it reduced internalised $^{59}$Fe uptake from $^{59}$Fe-Tf to 42% of the control in the BE-2 cell line (Table 2). In contrast, the activity of the 3 PCIH analogues were somewhat similar in all 3 cell lines, reducing $^{59}$Fe uptake from $^{59}$Fe-Tf to 15–38% of the control. The only exception to this was PCBBH, which was much less effective at reducing $^{59}$Fe uptake in SK-Mel-28 cells than either SK-N-MC or BE-2 cells (Table 2).

Effect of the PCIH Analogues on Cellular Proliferation

Figure 4:
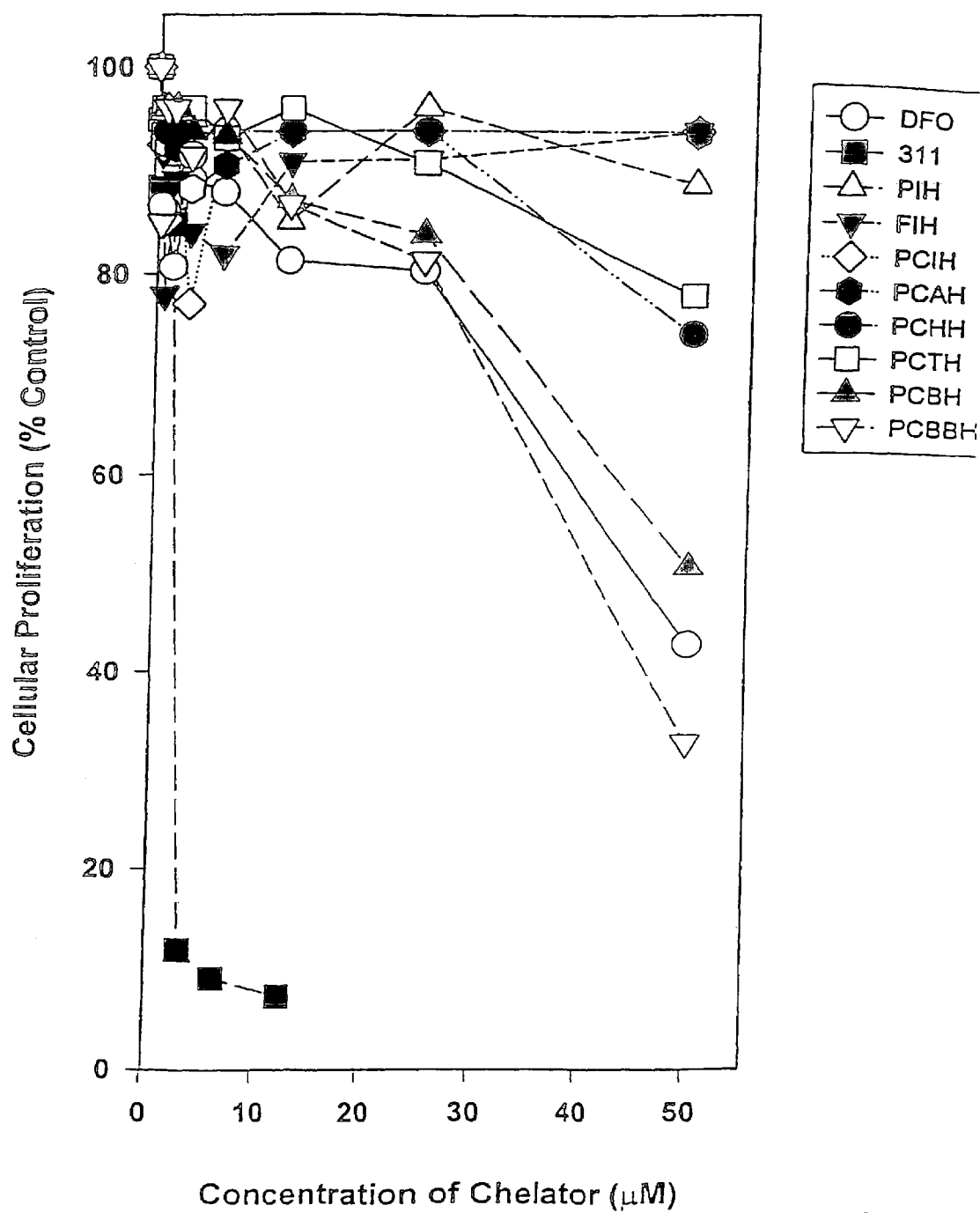
FIG. 4. The effect of chelator concentration on the proliferation of SK-N-MC neuroepithelioma cells. Cells were incubated in the presence and absence of the chelators (0–50 µM) for 90 h at 37° C. After this incubation period, cellular density was measured via the MTT assay. Each data point represents the mean of four replicates in a typical experiment of two experiments performed.

The studies above have clearly demonstrated that PCBH, PCBBH and PCTH have Fe chelation efficacy that is comparable to that of PIH or 311 and greater than that found for DFO. Hence, it was decided to determine the anti-proliferative effects of the PCIH analogues compared to DFO, PIH, and 311 whose activity has been previously characterized. From FIG. 4, it is clear that all of the PCIH analogues have much less effect on proliferation than chelator 311, which has been shown in previous studies to be potent at inhibiting the growth of a wide range of neoplastic cell lines. As shown previously, the ability of DFO to inhibit growth of SK-N-MC cells was far less than that of 311 ($IC_{50}$ DFO=47 μM; $IC_{50}$ 311=2 μM). Of the PCIH analogues, PCBBH and PCBH had anti-proliferative activity comparable to that of DFO ($IC_{50}$ PCBBH=42 μM; $IC_{50}$ PCBH=50 μM). The remaining PCIH analogues had little effect at inhibiting growth. It is of interest to note that while PIH, PCTH, PCBH and PCBBH had comparable Fe chelation activity to 311 in SK-N-MC cells (FIG. 2, Tables 1 and 2), their ability to inhibit proliferation was much less. These results concur with previous studies which demonstrated that Fe chelation efficacy is not always well correlated to the ability of a ligand to inhibit proliferation.

Effect of the Chelators on $^3$H-Thymidine, $^3$H-Leucine or $^3$H-Uridine Incorporation The effect of the chelators on $^3$H-thymidine, $^3$-leucine or $^3$H-uridine incorporation in to SK-N-MC cells was examined to obtain further information on the possible mechanisms of action of these ligands (Table 3). In these experiments, the effect of PCIH analogues have been compared to DFO and 311, as the anti-proliferative activity of these latter compounds has been previously characterized using SK-N-MC Cells. The PCIH analogues with the greatest Fe chelation efficacy, namely PCBBH, PCTH and PCBH, reduced $^3$H-thymidine incorporation to 33%, 64% and 72% of the control respectively, which was far less than the inhibition observed with 311 (0.1% of the control) and similar to that found with PIH (52% of the control). Interestingly, three chelators that showed little Fe chelation efficacy, namely, FIH, PCAH and PCHH (FIG. 2) caused a considerable decrease in $^3$H-thymidine incorporation to 11–17% of the control value (Table 3).

Table 3. The effect of the chelators on $^3$H-thymidine, $^3$H-leucine, or $^3$H-uridine incorporation into SK-N-MC neuroepithelioma cells. Cells were incubated for 20 hr at 37° C. with either DFO (100 μM) or the other chelators (50 μM). Following this, either $^3$H-thymidine, $^3$H-leucine, or $^3$H-uridine (1 μCi/mL) were added and the cells incubated for an additional 2 h at 37° C. (see Methods for details). Results are Mean±SD (4–5 determinations) from a typical experiment of 2–4 experiments performed.

|          | % Control                |                        |                        |
| -------- | ------------------------ | ---------------------- | ---------------------- |
| Chelator | $^3$H-Thymidine          | $^3$H-Leucine          | $^3$H-Uridine          |
| Control  | 100 ± 7                  | 100 ± 7                | 100 ± 2                |
| DFO      | 29 ± 13                  | 9 ± 0.7                | 34 ± 5                 |
| 311      | 0.1 ± 0.1                | 2 ± 0.3                | 5 ± 2                  |
| PIH      | 52 ± 9                   | 84 ± 5                 | 56 ± 9                 |
| PCIH     | 43 ± 0.5                 | 74 ± 7                 | 50 ± 8                 |

-continued

| Chelator | % Control | | |
|---|---|---|---|
| | $^3$H-Thymidine | $^3$H-Leucine | $^3$H-Uridine |
| PCTH | 64 ± 14 | 21 ± 6 | 43 ± 2 |
| PCBH | 72 ± 16 | 30 ± 13 | 31 ± 9 |
| PCBBH | 33 ± 8 | 16 ± 5 | 47 ± 2 |
| FIH | 17 ± 4 | 78 ± 5 | 48 ± 10 |
| PCAH | 12 ± 1 | 76 ± 2 | 40 ± 9 |
| PCHH | 11 ± 2 | 80 ± 10 | 41 ± 11 |

Examining the effect of the chelators at inhibiting $^3$H-leucine and $^3$H-uridine incorporation (Table 3), again the most effective chelator was 311, which reduced their incorporation to 2% and 5% of the control value respectively. In contrast, PCBH, PCBBH and PCTH, were far less active than 311 at inhibiting $^3$H-leucine and $^3$H-uridine incorporation, reducing it to 16–47% of the control (Table 3). DFO was also less effective than 311 at inhibiting $^3$H-leucine and $^3$H-uridine incorporation, reducing it to 9% and 34% of the control respectively. The 3 PCIH analogues that caused a considerable decrease in $^3$H-thymidine incorporation (FIH, PCAH and PCHH) did not inhibit $^3$H-leucine and $^3$H-uridine incorporation to the same extent, reducing it to between 40–80% of the control value (Table 3).

The Effect of Chelators on the RNA-Binding Activity of the Iron Regulatory Proteins (IRPs)

Figure 2:
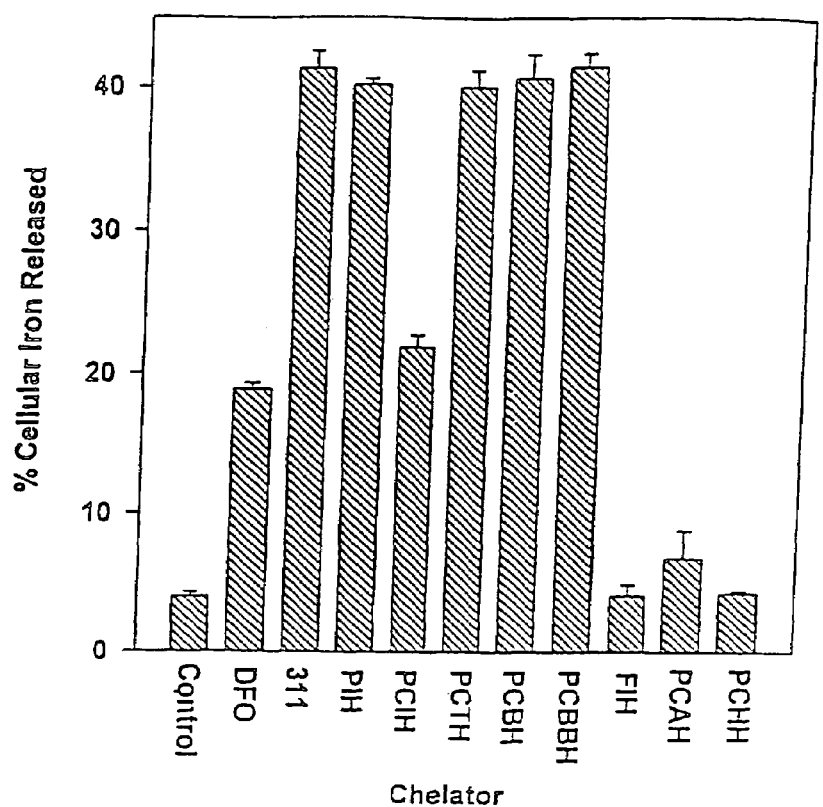
FIG. 2. The effect of DFO, 311, PIH, or the PCIH analogues on (A) $^{59}$Fe release from prelabelled SK-N-MC cells, and (B) $^{59}$Fe uptake from $^{59}$Fe-transferrin ($^{59}$Fe-Tf) by SK-N-MC cells. (A) SK-N-MC neuroepithelioma cells were labeled with $^{59}$Fe-Tf (0.75 µM) for 3 h at 37° C. washed, and then reincubated for 3 h at 37° C. in the presence of medium alone (control) or medium containing DFO (100 µM) or the other chelators (50 µM). (B) SK-N-MC cells were incubated for 3 h in media containing $^{59}$Fe-Tf (0.75 µm) and either DFO (100 µM) or the other chelators (50 µM), washed, and then incubated with pronase (1 mg/ml) for 30 min at 4° C. Results are expressed as the mean±SD of 3 replicates in a typical experiment of two experiments performed.
Figure 2:
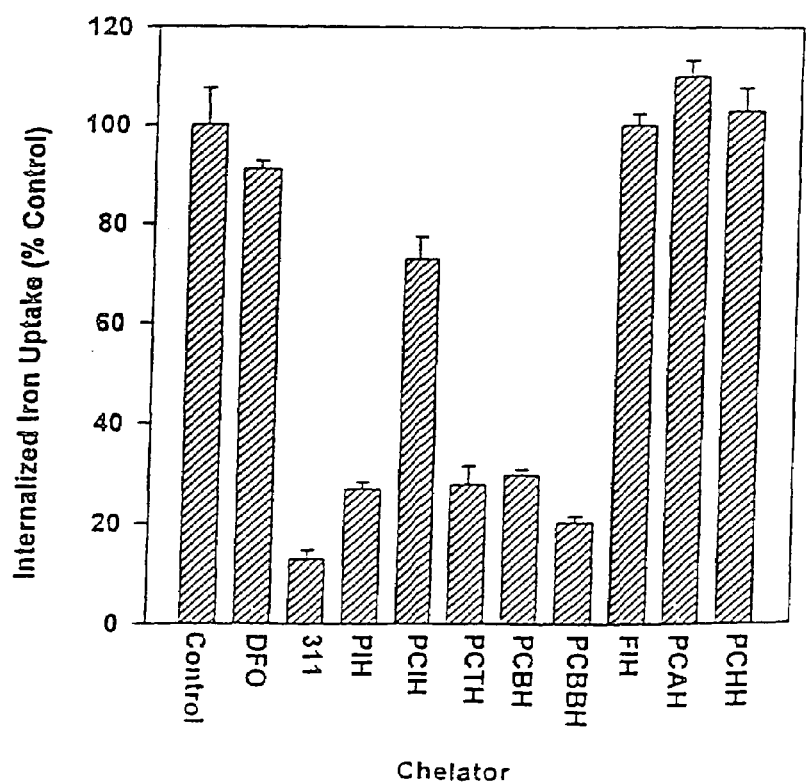
Figure 3:
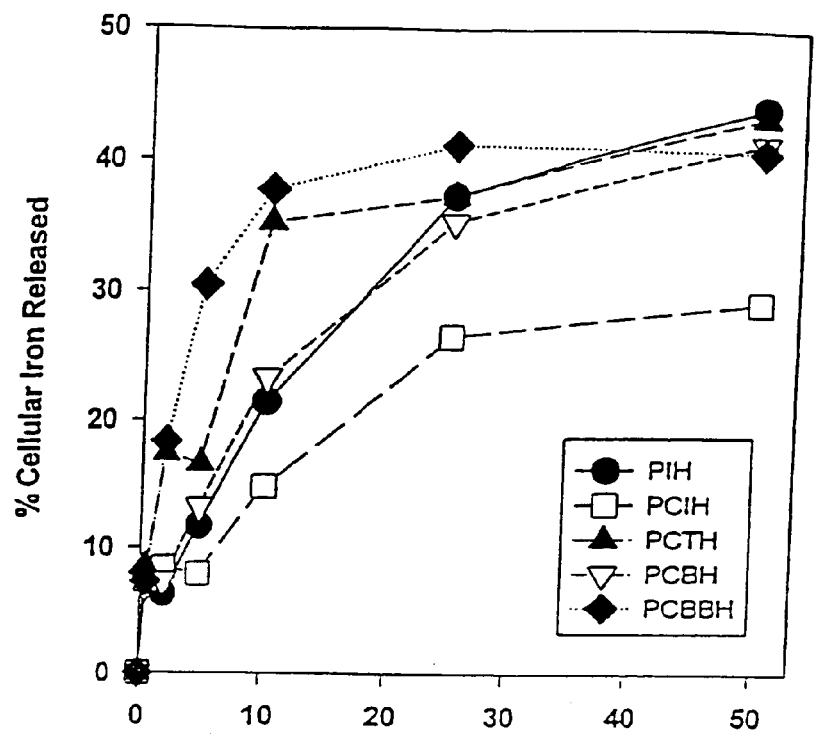
FIG. 3. The effect of chelator concentration on (A) iron release from prelabelled SK-N-MC cells and (B) $^{59}$Fe uptake from $^{59}$Fe-transferrin ($^{59}$Fe-Tf) by SK-N-MC cells. (A) SK-N-MC neuroepithelioma cells were labeled with $^{59}$Fe-Tf (0.75 µM) for 3 h at 37° C., washed, and then reincubated for 3 h at 37° C. in the presence of the chelators (0.5–50 µM). (B) SK-N-MC cells were incubated for 3 h in media containing $^{59}$Fe-Tf (0.75 µM) and the chelators (0.5–50 µM), washed, and then incubated with pronase (1 mg/ml) for 30 min at 4° C. Results are expressed as the mean of three replicates in a typical experiment of two experiments performed.
Figure 3:
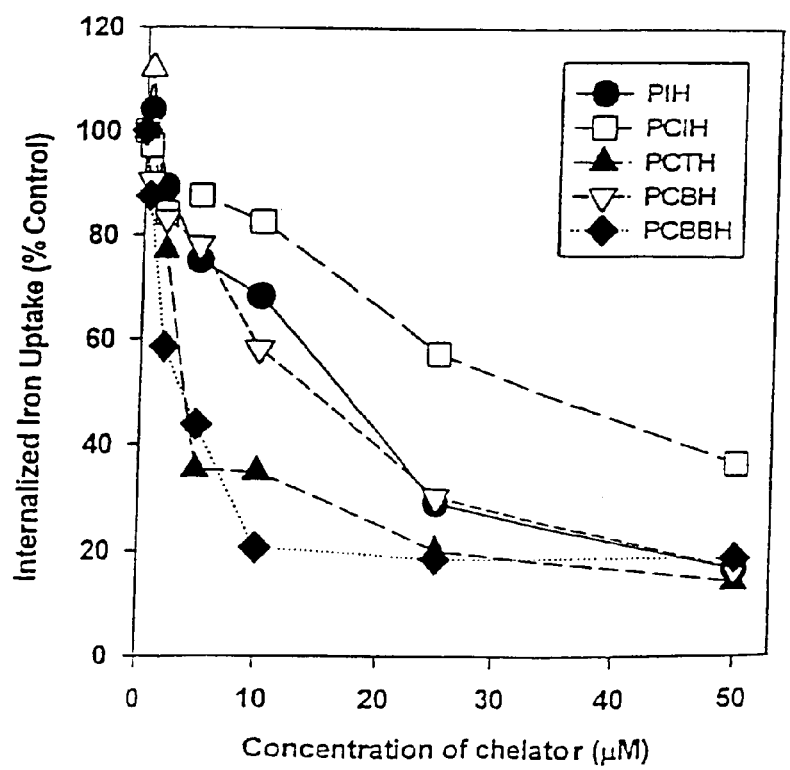
Figure 5:
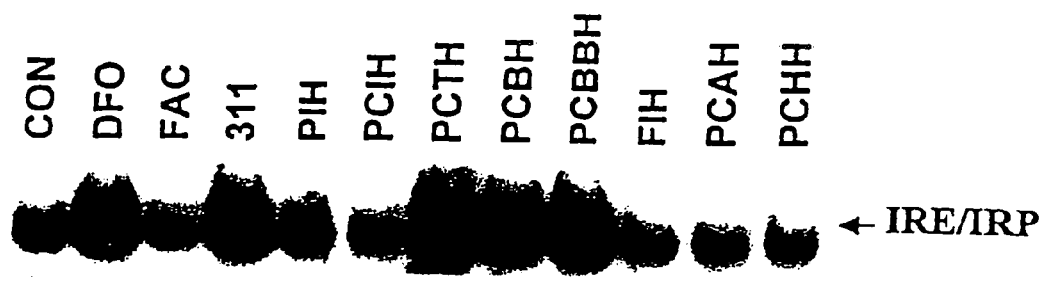
FIG. 5. The effect of the chelators on the RNA-binding activity of the iron-regulatory proteins (IRPs) in the SK-N-MC neuroepithelioma cells. Cells were incubated for 20 h with either medium alone (control), ferric ammonium citrate (FAC: 100 µg/ml), DFO (100 µM), or the other chelators (25 µM). The result illustrated is a typical experiment from two experiments performed.

An important effect of intracellular Fe depletion using DFO is the activation of RNA-binding activity of the iron regulatory proteins (IRP's) (Hentze et al., 1996, Proc. Natl. Acad. Sci. USA 93 8175–82). While the effect of DFO on the RNA-binding activity of this protein has been well characterized, little is known concerning the effect of other Fe chelators such as the PCIH analogues. The present inventors examined the effect of a 20 hr incubation with 311, PIH and the PCIH analogues (25 µM) on IRP-RNA binding activity in SK-N-MC cells. In all experiments, DFO (100 µM) was used as a positive control to deplete cells of Fe and increase IRP-RNA binding activity. In contrast, ferric ammonium citrate (FAC: 100 µg/ml) was used to donate Fe to cells and reduce IRP-RNA binding. Examining FIG. 5, it is clear that only one major IRP-IRE band is present, which is due to the fact that human IRP1-IRE and IRP2-IRE complexes co-migrate in non-denaturing polyacrylamide gels (Chitambar et al., 1995, Cancer Res. 55 4361–66). As expected, there was an increase in IRP-RNA binding activity following a 20 hr incubation with DFO, whereas after a 20 hr incubation with the Fe donor FAC, there was an appreciable decrease in IRP-RNA binding activity compared to the control (FIG. 5). In comparison to the control, there was a marked increase in IRP-RNA binding activity after treatment of cells with 311, PCTH, PCBH and PCBBH (FIG. 5), which most likely reflects their high Fe chelation efficacy (FIGS. 2 and 3). Surprisingly, PIH and PCIH had little effect on IRP-RNA binding activity, whereas FIH, PCAH and PCHH decreased IRP-RNA binding compared to the control (FIG. 5). Addition of β-mercaptoethanol to the cell lysates demonstrated that there was no change in the total amount of IRP-RNA binding activity after incubation with the chelators (date not shown).

Figure 6:
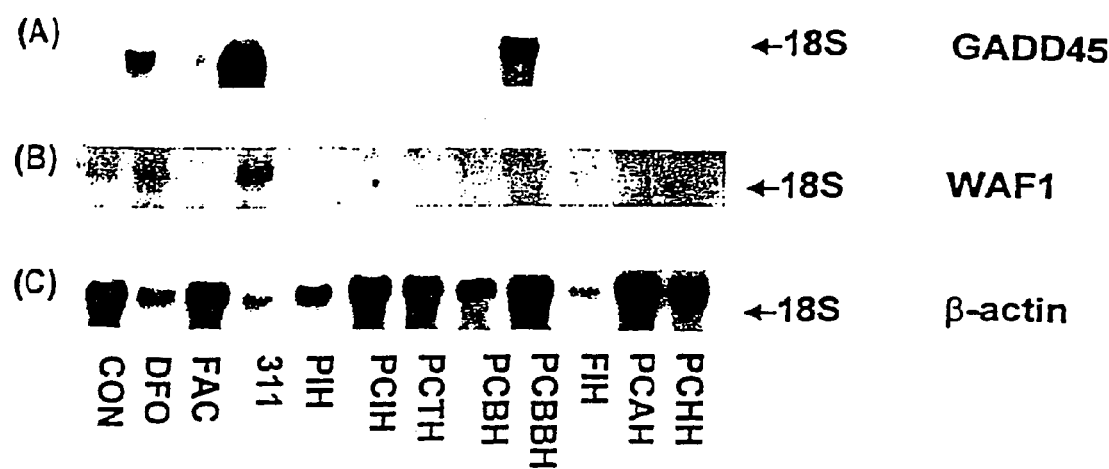
FIG. 6. The effect of the chelators on mRNA levels of GADD45, WAF1 and β-actin in SK-N-MC neuroepithelioma cells. Total RNA was extracted from cells after a 20 h incubation with medium alone (control) or medium containing ferric ammonium citrate (100 µg/mL), DFO (100 µM), or the other chelators (25 µM). The isolated RNA was then electrophoresed on a 1.2% agarose-formaldehyde gel, transferred to a hybridisation membrane, and probed under high stringency conditions. The result illustrated is a typical experiment from three experiments performed.

Effect of the PCIH Analogues on the Expression of Genes Involved in the Cell Cycle Treatment of cells with high concentrations of DFO (150 µM) or much lower concentrations of 311 (2.5–5 µM) resulted in an increase in the expression of the p53-responsive genes WAF1 (wild-type activating gene 1) and GADD45 (growth arrest and DNA damage gene: (Darnell et al., 1994, Blood 94 781–792). WAF-1 is a potent universal inhibitor of cyclin-dependent kinases and can induce a $G_1/S$ arrest and possibly a $G_2/M$ arrest. GADD45 is induced upon DNA damage and can arrest the cell cycle and is also involved in DNA nucleotide excision repair. While it is known that DFO, 311 and other Fe chelators can cause cell arrest, little is understood concerning the changes in gene expression that may play a role in inhibiting the cell cycle. In the present study, incubation with 311 (25 µM) and to a lesser extent DFO (100 µM), caused an increase in the levels of both WAF1 and GADD45 mRNA in SK-N-MC cells (FIG. 6). Of the PCIH analogues, only PCBBH markedly increased the level of GADD45 mRNA but not WAF1 mRNA. This latter effect corresponds to the greater antiproliferative activity of PCBBH relative to the other PCIH analogues.

Effect of the PCIH Analogues on Mitochondrial Iron Mobilization in Reticulocytes In this investigation Fe chelation efficacy of PCIH analogues was studied using the only well characterised model of mitochondrial Fe overload, that is reticulocytes loaded with mitochondrial non-heme $^{59}$Fe. In all studies, PIH was used as the reference compound as this chelator has been characterized in previous studies to effectively deplete the non-heme mitochondrial Fe pool.

Figure 7:
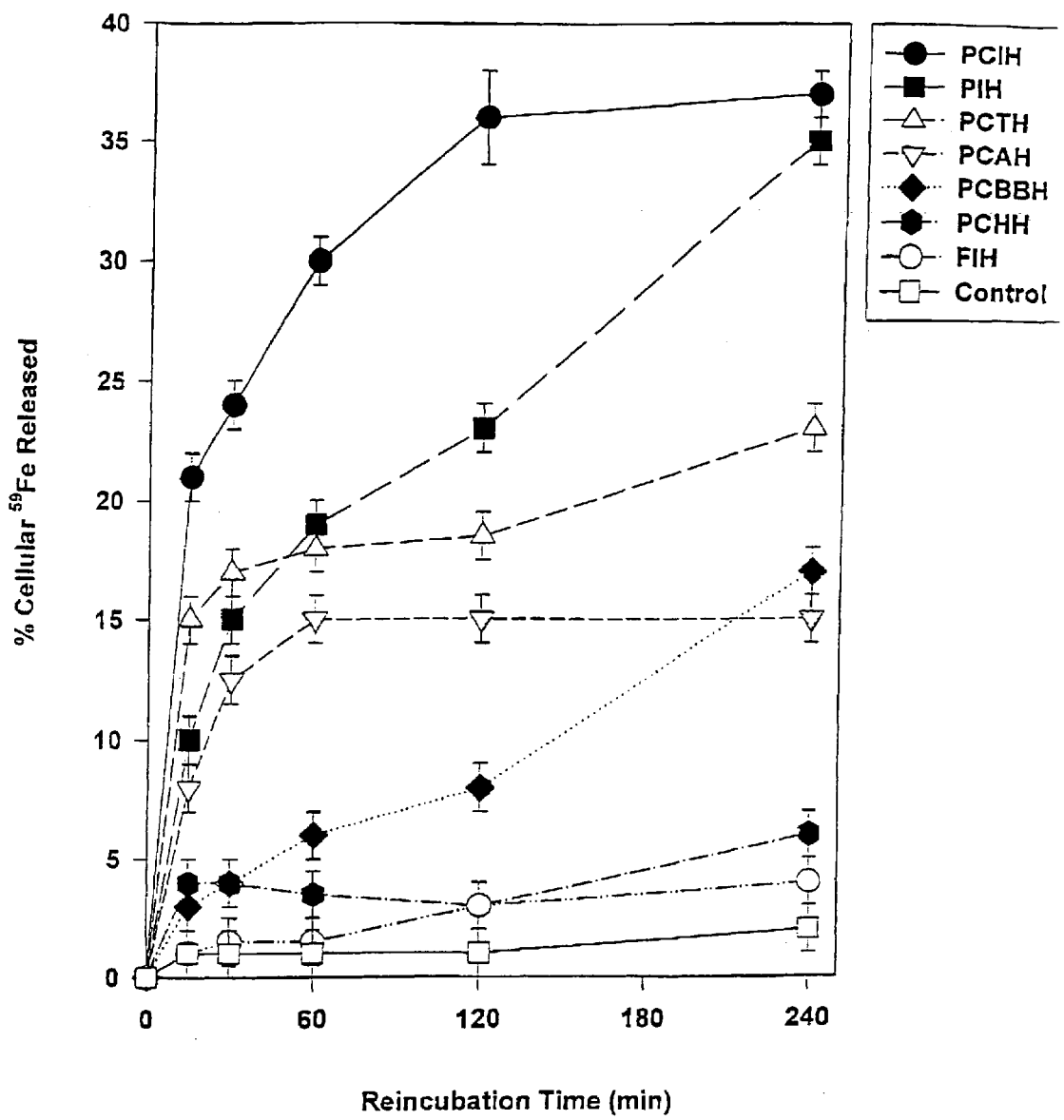
FIG. 7. The effect of reincubation time with the Fe chelators on $^{59}$Fe mobilization from $^{59}$Fe-loaded reticulocytes. The cells were labelled with $^{59}$Fe-transferrin (3.75 µM) in the presence of the heme synthesis inhibitor, succinylacetone (1 mM), and incubated with the cells for 1 h at 37° C. The $^{59}$Fe-labelled reticulocytes were then incubated with the chelators (200 µM) for 15–240 min at 37° C. The results are Mean±SD (3 determinations) in a typical experiment of three performed.

In initial studies the effect of reincubation time on $^{59}$Fe release from Fe-loaded reticulocytes was assessed (FIG. 7). In these experiments, cells were labelled with $^{59}$Fe-Tf for 1 h at 37° C., washed, and then reincubated for up to 240 min in the presence and absence of the chelators (200 µM). Of the eight compounds examined, PCIH was the most effective at increasing cellular $^{59}$Fe release as a function of incubation time (FIG. 7). Indeed, PCIH was more effective than PIH during incubation periods from 15–120 min, but had similar activity after a 240 min reincubation. The high activity of PCIH is evident after only 15 min incubation with $^{59}$Fe-loaded reticulocytes, at which point the compound has mobilized 21±1% (3 determinations) of cellular $^{59}$Fe (FIG. 7). The amount of $^{59}$Fe released by PCIH after 15 min was more than that mobilized by PCBBH, PCAH, PCHH, and FIH after 240 min of incubation viz. 17%, 15%, 6%, and 4% respectively. Examination of the ethanol-soluble intracellular $^{59}$Fe after incubation with the chelators revealed that this only increased in the presence of FIH (FIG. 8), suggesting the possible accumulation of its $^{59}$Fe complex within the cell.

Figure 8:
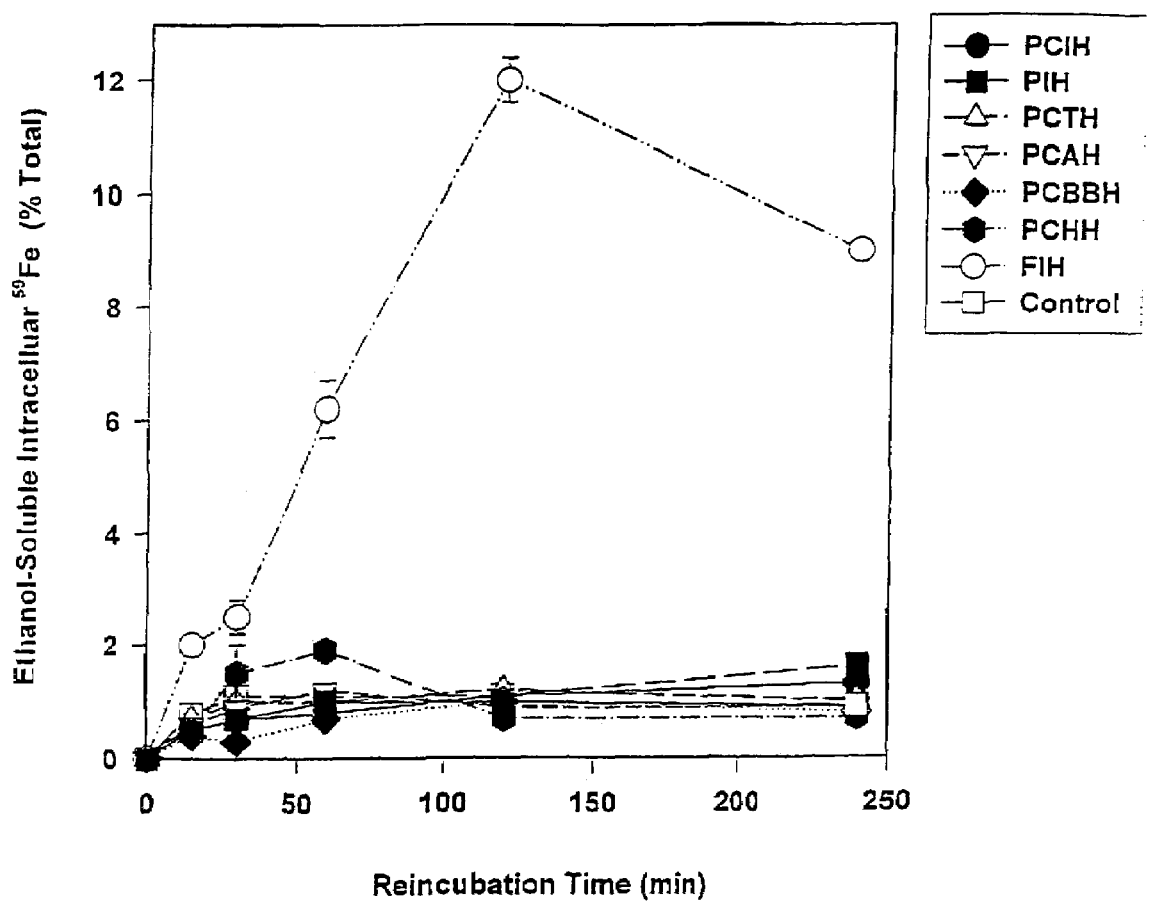
FIG. 8. The effect of reincubation time with the Fe chelators on the percentage of ethanol-soluble $^{59}$Fe in reticulocytes. The cells were treated as in FIG. 7 and the percentage of ethanol-soluble $^{59}$Fe determined by lysing $^{59}$Fe-labelled reticulocytes with ice-cold water. The proteins precipitated ice-cold 95% ethanol and soluble and insoluble fractions separated by centrifugation (see Methods for details). The results are Mean±SD (3 determinations) in a typical experiment of three performed.
Figure 9:
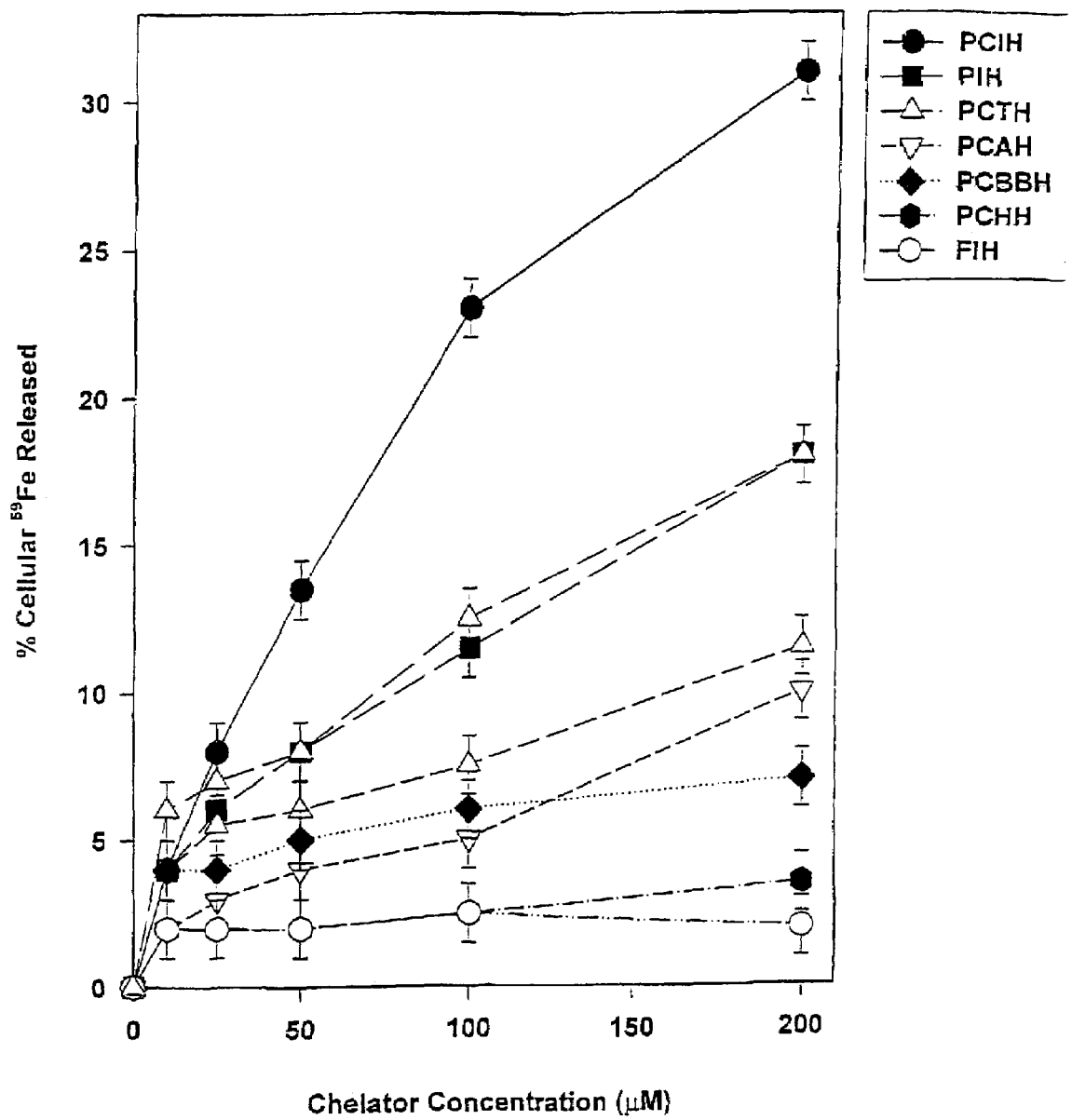
FIG. 9. The effect of chelator concentration on $^{59}$Fe mobilization from $^{59}$Fe-loaded reticulocytes. The cells were labelled with $^{59}$Fe-transferrin (3.75 µM) in the presence of the heme synthesis inhibitor, succinylacetone (1 mM), and incubated with the cells for 1 h at 37° C. The $^{59}$Fe-labelled reticulocytes were then incubated with the chelators (10–200 µM) for 15–240 min at 37° C. The results are Mean±SD (3 determinations) in a typical experiment of three performed.

In further studies, the effect of chelator concentration was assessed on $^{59}$FE mobilization from $^{59}$Fe-loaded reticulocytes. In these experiments, the cells were labelled with $^{59}$Fe-Tf for 1 h at 37° C., washed, and then reincubated for 1 h at 37° C. in the presence and absence of the chelators (FIG. 9). Again, PCIH was the most active compound. At a concentration of 200 µM, PCIH released 31±1% (3 determinations) of cellular $^{59}$Fe compared to PIH that mobilized 18±1% (3 determinations). The compound PCTH had similar Fe chelation efficacy as PIH, while the remaining ligands were substantially less efficient. As described previously, DFO even at high concentrations up to 5 mM had little effect on mobilizing $^{59}$Fe, having activity similar to that observed with control medium. As reported using the SK-N-MC neuroepithelioma cell line, both FIH and PCHH showed very low activity at mobilizing intracellular $^{59}$Fe (FIG. 9). As shown in FIG. 8, an increase in ethanol-soluble intracellular $^{59}$Fe was only observed with FIH and this increased as the concentration increased up to 200 µM.

CONCLUSIONS

The present inventors have synthesized and screened a number of aroylhydrazone ligands based upon 2-pyridylcarboxaldehyde isonicotinoyl hydrazone (PCIH). Three of these chelators, namely PCBH, PCBBH and PCTH, showed Fe chelation activity that was greater than DFO and comparable to that of PIH and 311. In addition, the anti-proliferative activity of these chelators was far less than that found for analogue 311, an aroylhydrazone ligand previously shown to possess high cytotoxic activity. These properties suggest that these three PCIH analogues would be more appropriate for the treatment of Fe-loading diseases rather than as anti-proliferative agents against cancer.

It was attempted to synthesize ligands with high anti-proliferative activity by condensing 2-pyridylcarboxaldehyde with a range of acid hydrazides previously used in the synthesis of the PIH analogues. The 2-pyridylcarboxaldehyde moiety was examined because when it is condensed with thiosemicarbazide to form the relevant thiosemicarbazone, this ligand has potent anti-proliferative activity. In fact, this latter group of α-N-heterocyclic carboxaldehyde thiosemicarbazones have been described as the most effective ribonucleotide reductase inhibitors yet identified. The present results demonstrate that the PCIH analogues show little anti-proliferative activity being far less effective than 311. These data may indicate that in contrast to the 2-pyridylcarboxaldehyde moiety, the thiosemicarbazide component of the 2-pyridylcarboxaldehyde thiosemicarbazones may be important for anti-proliferative activity.

All of the PCIH analogues examined in the present investigation, except FIH, have the same potential Fe ligating sites, namely the carbonyl oxygen, aldimine nitrogen and 2-pyridyl nitrogen (FIG. 1). It is of interest, however, that the biological activity of these ligands can be markedly influenced by the nature of the substituents placed distal to the Fe-binding site. For example, both PCHH and PCAH display very poor Fe chelation activity, while PCTH, PCBBH and PCBH show very high efficacy (FIGS. 2A, 2B). Since lipophilicity is an important criterion for the membrane permeability and Fe chelation efficacy of ligands, it may be that the increased hydrophilicity of PCHH and PCAH (due to the presence of a hydroxyl and amino group respectively) could prevent the access of these chelators to intracellular Fe pools. While PCAH, PCHH and FIH showed little ability to mobilize $^{59}$Fe and inhibit $^{59}$Fe uptake from $^{59}$Fe-Tf, it was of interest that these chelators were more effective than the other PCIH analogues at inhibiting $^3$H-thymidine incorporation (Table 3). Considering this, it is possible that FIH, PCAH and PCHH may be relatively more efficient at inhibiting ribonucleotide reductase, a crucial Fe-containing enzyme that is involved in the conversion of ribonucleotides into deoxyribonucleotides for DNA synthesis.

One advantage of the PCIH analogues according to the present invention in comparison to the PIH analogues was their higher solubility in aqueous solutions. While lipophilicity is an important property for membrane permeability, the solubility of a chelator in water is also an important factor in terms of its practical and clinical use. Hence, for a chelator to be employed as a useful therapeutic agent, an appropriate balance between solubility in aqueous solutions and the ability to permeate biological membranes must be reached. For several of the PCIH analogues, this appears to have been achieved.

The effect of DFO at increasing the RNA-binding activity of the IRPs has been well characterized. Little is known, however, concerning the effect of other Fe chelators. The fact that 311, PCTH, PCBH and PCBBH all increased IRP-RNA binding activity in a similar way to DFO (FIG. 5) may suggest that these ligands act on the same or a similar intracellular pool of Fe. In contrast to expectations, PIH and PCIH had no effect at increasing IRP-RNA binding activity despite the fact that these chelators were highly effective at mobilizing $^{59}$Fe from cells and preventing $^{59}$Fe uptake from $^{59}$Fe-Tf (FIGS. 2 and 3). Higher concentrations of PIH did increase IRP-RNA binding activity, however, suggesting that a concentration effect may be involved. It is also of interest to note that FIH, PCAH and PCHH inhibited IRP-RNA binding activity to a level comparable to that found after incubation with FAC (FIG. 5). Considering these results, it can be speculated that PCAH, PCHH and FIH may disturb the intracellular distribution of Fe, such that there is an increase in the Fe pool sensed by the IRPs.

While ability of Fe chelators to inhibit the cell cycle at $G_1/S$ is well known, very little is understood about the changes in gene expression that may play a role in this process. In a previous study using neuroblastoma cell lines and K562 cells, the present inventors demonstrated that incubation with DFO (150 µM) or 311 (2.5–5 µM) resulted in a marked increase in the expression of WAF1 and GADD45, two molecules that play key roles in inducing cell cycle arrest at $G_1/S$. In the present study, it has been confirmed these results using DFO and 311 and have shown that of the PCIH analogues, only PCBBH increased the expression of GADD45 RNA (FIG. 6). The ability of a chelator to increase the expression of molecules involved in inhibiting the cell cycle is not an appropriate characteristic of a compound to be used of treating Fe overload.

Considering this, and the fact that PCBBH was the most effective ligand at inhibiting proliferation. PCTH and PCBH appear to be preferable candidate chelators for the treatment of Fe-loading diseases.

In the present work, all of the PCIH analogues showed far less anti-proliferative activity than 311 (see FIG. 4), despite the high Fe chelation efficacy of some of these compounds, e.g. PCBBH, PCBH and PCTH (FIGS. 2 and 3). The present inventors have shown that when the Fe complex of 311 is prepared, it prevents its anti-proliferative activity and also its ability to increase the expression of GADD45 and WAF1 mRNA. These results together with its high Fe chelation efficacy, suggest that 311 inhibits growth by depleting intracellular Fe pools.

Several studies have suggested that Friedreich's ataxia may be caused by an accumulation of Fe in the mitochondrion. If this latter disease is caused by mitochondrial Fe overload, possible treatment regimes could include Fe chelation therapy. DFO effectively depletes cytosolic Fe pools, but is unknown whether it can chelate mitochondrial Fe. In contrast, previous studies have shown that aroylhydrazone chelators, such as PIH, can remove Fe from the mitochondrion.

It will also be apparent that the PCIH analogues according to the present invention may also include these compounds in their free base form as well as their hydrochloride salts and the synthesis of the bases and salts is discussed hereinafter.

At present, there is no treatment for FA which is a severe crippling neurological condition. The exciting finding that mitochondrial Fe accumulation may play an important role in its pathogenesis suggests that a possible therapeutic intervention may be Fe chelation therapy. This study identifies some of the PCIH class of chelators as highly effective ligands for mobilizing mitochondrial non-heme Fe from reticulocytes. This latter model was implemented as it is the only well characterized system of mitochondrial Fe overload in cells. The ability of PCIH and PCTH to mobilize mitochondria Fe pools overcomes the disadvantages of DFO that cannot effectively deplete Fe from this compartment. These studies complement the work demonstrating the high chelation efficacy and low toxicity of the PCIH group of ligands in the SK-N-MC neuroepithelioma cell line. Indeed, some of these compounds were far more efficient than DFO at increasing Fe mobilization from cells and preventing Fe uptake from Tf.

The PCIH class of chelators were specifically designed based upon studies on a wide range of compounds of the PIH class. From these studies, structural features necessary for high Fe chelation efficacy and low toxicity were chosen to optimise the use of these ligands as agents to treat Fe-overload disease. Indeed, the design strategy has been very successful, as it has resulted in chelators that show higher activity than the parent compound PIH.

The strategy to design new chelators derived from PIH was based upon the advantageous properties of this compound. These are: (a) oral effectiveness; (b) near optimal hydrophilic-lipophilic balance; (c) high specificity and selectivity for Fe; (d) predominantly neutral at physiological pH; (e) economical and simple to synthesize; and (f) high chelation efficacy both in vitro and in vivo.

The reason for the ability of some of the PCIH ligands to mobilize mitochondrial Fe may be their much higher lipophilicity in comparison to DFO. Indeed, to permeate the mitochondrion and chelate Fe, three lipid membranes need to be transversed, viz., the plasma membrane and the inner and outer mitochondrial membranes. Accordingly, a lipophilic chelator that rapidly permeates membranes and targets mitochondrial Fe will be far more effective than a hydrophilic compound such as DFO. This may be an important property of the analogue, since the Fe-loading in FA is not pronounced as that found in untreated β-thalassemia. Hence, only very short durations of therapy may be possible or necessary in order to prevent overall mitochondrial Fe pools could be an important property.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A 2-pyridylcarboxaldehyde isonicotinoyl hydrazone (PCIH) analogue suitable for use as an in vivo iron chelator, the PCIH analogue having Formula 1:

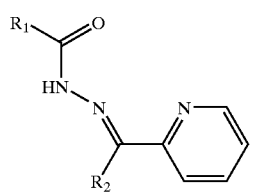

Formula 1 wherein R2 is either OH or H such that when R2 is OH R1 is a phenyl, pyridine, furan or thiophene ring optionally with alkyl, halo, nitro, amine, or hydroxyl attached to any of the vacant positions on the ring; isomers thereof; or salts thereof; or when R2 is H, R1 is 2-, 3- or 4-bromophenyl optionally substituted with alkyl, halo, nitro or amine attached to any of the vacant positions on the ring; or isomers or salts thereof.

2. The PCIH analogue according to claim 1 selected from the group consisting of 2-pyridylcarboxaldehyde m-bromobenzoyl hydrazone (PCBBH) salts thereof, and isomers thereof.

3. A pharmaceutical compositions suitable for use as an iron chelator comprising a therapeutically effective amount of at least one 2-pyridylcarboxaldehyde isonicotinoyl hydrazone (PCIH) analogue having Formula 1:

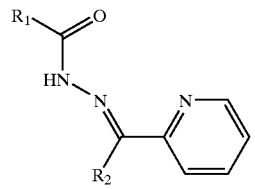

Formula 1 wherein R2 is either H or OH such that when R2 is OH R1 is a phenyl, pyridine, furan or thiophene ring optionally with alkyl, halo, nitro, amine, or hydroxyl attached to any of the vacant positions on the ring; isomers thereof or salts thereof; or when R2 is H, R1 is thiophene, 2-, 3- or 4-bromophenyl optionally substituted with alkyl, halo, nitro or amine attached to any vacant positions on the ring, phenol or aniline; or isomers or salts thereof; together with a pharmaceutically suitable carrier or diluent.

4. The pharmaceutical composition according to claim 3 wherein the 2-pyridylcarboxaldehyde isonicotinoyl hydrazone (PCIH) analogue is selected from the group consisting of 2-pyridylcarboxaldehyde 2-thiophenecarboxyl hydrazone (PCTH), 2-pyridylcarboxaldehyde m-bromobenzoyl hydrazone (PCBBH), 2-pyridylcarboxaldehyde p-aminobenzoyl hydrazone (PCAH), 2-pyridylcarboxaldehyde p-hydroxy benzoyl hydrazone (PCHH), salts thereof, and isomers thereof.

5. The pharmaceutical composition according to claim 3 formulated for subcutaneous or intravenous injection, oral administration, inhalation, transdermal application, or rectal administration.

6. A method of iron chelation therapy comprising administering to a patient a pharmaceutical composition comprising a therapeutically effective amount of at least one 2-pyridylcarboxaldehyde isonicotinoyl hydrazone (PCIH) analogue having Formula 1:

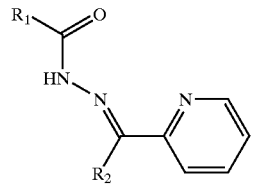

Formula 1 wherein R1 is a phenyl, pyridine, furan or thiophene ring optionally with alkyl, halo, nitro, amine, or hydroxyl attached to any of the vacant positions on the ring, and R2 is either H or OH, isomers thereof or salts thereof, together with a pharmaceutically suitable carrier or diluent.

7. The method according to claim 6 wherein the pharmaceutical composition is administered in a dosage regimen of 30–500 mg per kg of body weight of the patient.

8. The method according to claim 7 wherein the dosage regimen is 50–100 mg per kg of body weight.

9. The method according to claim 6 wherein the patient suffers from iron-overload.

10. The method according to claim 9 wherein the patient suffers from β-thalassemia or Friedreich's ataxia.

* * * * *